(12) United States Patent
Hagihara et al.

(10) Patent No.: US 10,982,186 B2
(45) Date of Patent: *Apr. 20, 2021

(54) CELL CULTURING METHOD AND KIT

(71) Applicant: UBE INDUSTRIES, LTD., Ube (JP)

(72) Inventors: Masahiko Hagihara, Ube (JP); Motohisa Shimizu, Ube (JP); Yukinori Wada, Ube (JP)

(73) Assignee: UBE INDUSTRIES, LTD., Yamaguchi (JP)

( * ) Notice: Subject to any disclaimer, the term of this patent is extended or adjusted under 35 U.S.C. 154(b) by 585 days.

This patent is subject to a terminal disclaimer.

(21) Appl. No.: 15/880,443

(22) Filed: Jan. 25, 2018

(65) Prior Publication Data

US 2018/0155679 A1 Jun. 7, 2018

Related U.S. Application Data

(62) Division of application No. 15/545,234, filed as application No. PCT/JP2016/052219 on Jan. 26, 2016, now Pat. No. 10,738,277.

(30) Foreign Application Priority Data

Jan. 26, 2015 (JP) .............................. JP2015-012738
Jan. 26, 2015 (JP) .............................. JP2015-012852

(51) Int. Cl.
| | | |
|---|---|---|
| *C12N 5/00* | (2006.01) | |
| *C12N 1/20* | (2006.01) | |
| *C12N 1/16* | (2006.01) | |
| *C12N 1/00* | (2006.01) | |
| *C12M 1/12* | (2006.01) | |

(52) U.S. Cl.
CPC ............ *C12N 5/0068* (2013.01); *C12M 25/02* (2013.01); *C12M 25/14* (2013.01); *C12N 1/00* (2013.01); *C12N 1/16* (2013.01); *C12N 1/20* (2013.01); *C12N 2533/30* (2013.01); *C12N 2535/00* (2013.01)

(58) Field of Classification Search
CPC .................................................. C12N 5/0068
USPC ......................................................... 435/350
See application file for complete search history.

(56) References Cited

U.S. PATENT DOCUMENTS

| | | |
|---|---|---|
| 2009/0042288 A1 | 2/2009 | Stoppini |
| 2011/0281351 A1 | 11/2011 | Adachi et al. |
| 2011/0318556 A1 | 12/2011 | Ohya et al. |

FOREIGN PATENT DOCUMENTS

| | | |
|---|---|---|
| CA | 2 568 646 A1 | 12/2005 |
| CA | 2 974 276 A1 | 8/2016 |
| CN | 103710263 A | 4/2014 |
| JP | 63-196286 A | 8/1988 |
| JP | H5-335368 A | 12/1993 |
| JP | H7-313151 A | 12/1995 |
| JP | 2001-190270 A | 7/2001 |
| JP | 2003-180337 A | 7/2003 |
| JP | 2004-173563 A | 6/2004 |
| JP | 2004-344002 A | 12/2004 |
| JP | 2008-543303 A | 12/2008 |
| JP | 2011-219585 A | 11/2011 |
| JP | 2011-219586 A | 11/2011 |
| JP | 5460241 B2 | 4/2014 |
| JP | 5549209 B2 | 7/2014 |
| JP | 2015-213498 A | 12/2015 |
| WO | 2005/121311 A1 | 12/2005 |
| WO | 2010/038873 A1 | 4/2010 |
| WO | 2010/087397 A1 | 8/2010 |
| WO | 2015/012415 A1 | 1/2015 |

OTHER PUBLICATIONS

Maenosono, Hirotaka et al., "A Transparent Polyimide Film as a Biological Cell Culture Sheet with Microstructures," *Journal of Biomaterials and Nanobiotechnology* (2014; accepted Dec. 28, 2013); 5:17-23.

Subrizi et al., "Generation of hESC-derived retinal pigment epithelium on biopolymer coated polyimide membranes," Biomaterials, 33:8047-8053 (2012).

International Search Report dated Mar. 8, 2016 corresponding to International Patent Application No. PCT/JP/2016/052219, filed on Jan. 26, 2016; 2 pages.

Otsuji, Tomomi G. et al., "A 3D Sphere Culture System Containing Functional Polymers for Large-Scale Human Pluripotent Stem Cell Production," *Stem Cell Reports* (May 6, 2014); 2:734-745.

*Primary Examiner* — James D Schultz
*Assistant Examiner* — Alexander W Nicol
(74) *Attorney, Agent, or Firm* — Mintz Levin Cohn Ferris Glovsky and Popeo PC

(57) ABSTRACT

The present invention relates to a cell culturing method and kit. More specifically, it relates to a cell culturing method and kit using a support that is exposed to the air. It further relates to a method of culturing cells by allowing them to migrate onto a porous polyimide film.

17 Claims, 12 Drawing Sheets

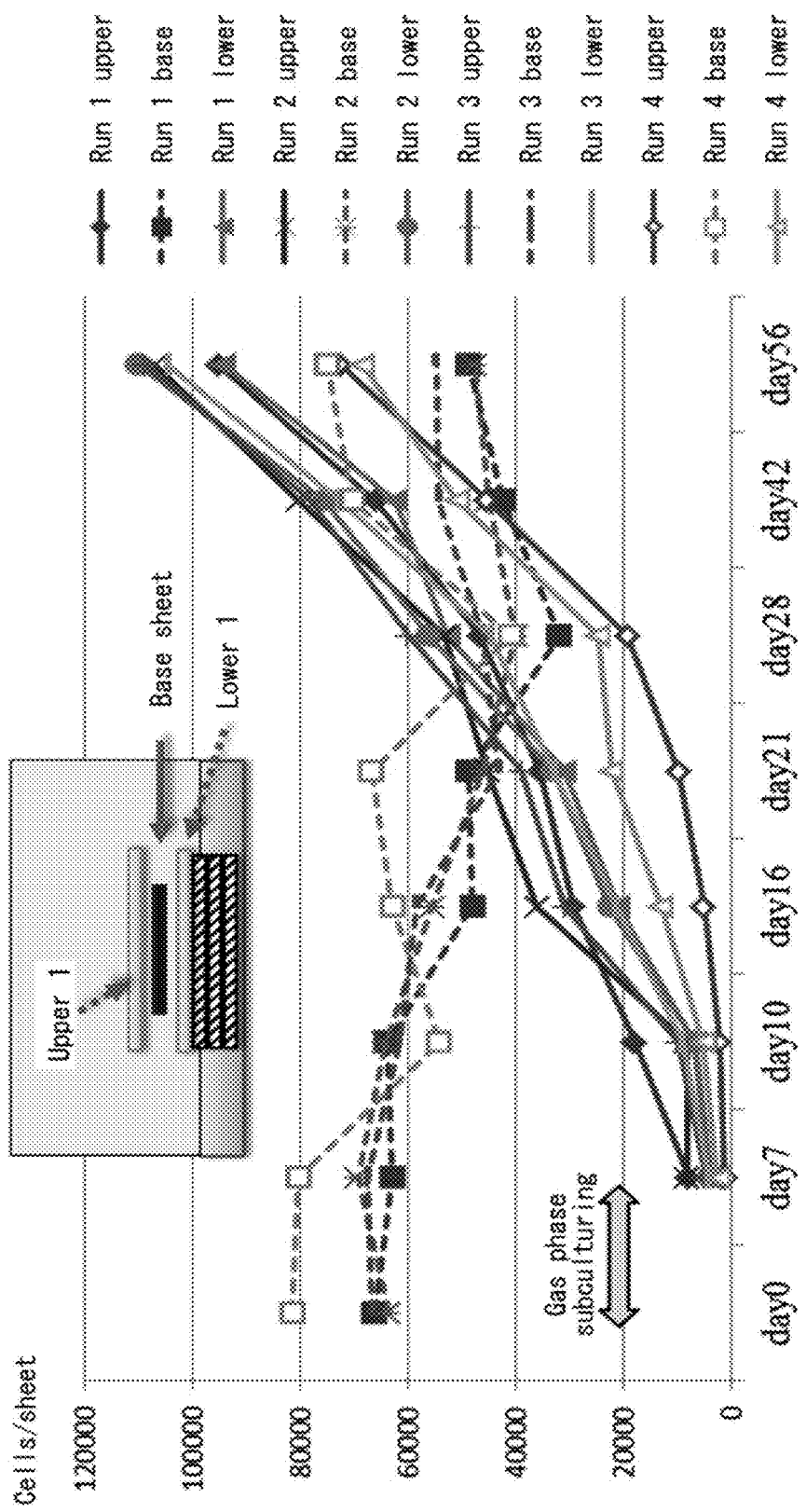

CELL CULTURING METHOD AND KIT

TECHNICAL FIELD

The present invention relates to a cell culturing method and kit. More specifically, it relates to a cell culturing method and kit using a support that is exposed to the air. It further relates to a method of culturing cells by allowing them to migrate onto a porous polyimide film.

BACKGROUND ART

Cell Culturing

Cells generally exist as three-dimensional aggregates in the body, but in classical plate culturing, cells are cultured in a monolayer fashion with the cells attached to a vessel. Numerous reports have indicated significant differences in cell properties with different culturing environments. An alternative is suspension culturing in which cells are cultured in a liquid culturing medium, but some cells are suited for suspension culture while others are not.

In recent years, with increasing interest being directed toward cultured cell-based production of vaccines, and in vivo proteins such as enzymes, hormones, antibodies and cytokines, as well as cell grafts for use in regenerative medicine, greater focus has been placed on efficient and convenient methodologies for mass cell culturing. In cell culturing, regardless of whether or not a cell culture support is used and regardless of whether suspended cells or adherent cells are used, supply of oxygen is an essential issue for achieving healthy growth of the cells, with the exception of anaerobic bacteria. For example, when adherent cells are plate cultured using a dish, a plate or a chamber, there are restrictions on the proper range for the medium volume with respect to the area of the culturing vessel. Therefore, when an excessive amount of medium has been used, it is often the case that oxygen may be insufficiently supplied to the cells and the low oxygen condition may lead to inhibition or even cell death. Moreover, with spheroid-forming cell population, an excessively large size is known to result in oxygen deficiency for the cells in the interior (NPL 1). As a solution for the issue of oxygen supply, it has been attempted to increase the oxygen concentration by utilizing microbubbles (PTL 1) or to employ methods for uniformly supplying oxygen in microcarrier culturing (PTL 2).

Methods of culturing while exposing the cell culture support to a gas phase have also been attempted. For example, for hollow fiber culturing, a liquid phase/gas phase exposure bioreactor has been proposed (PTL 3), as a system wherein hollow fibers inhabited by cells are rotated for alternate exposure to a gas phase and a liquid phase. There has also been proposed a system for cell culturing wherein a support sheet with an excellent handling property is entirely exposed to a gas phase (PTL 4), although no particular embodiment has been specified.

If a support can be exposed to a gas phase during cell culturing, then the issue of oxygen supply for cell culturing will be greatly improved and a very attractive methodology will be provided toward establishing a more efficient culturing method. However, since it is impossible to avoid drying out of fibrous materials that are used as known cell culture supports, a demand exists for establishing a novel "culturing method that allows the support to be exposed to a gas phase", and that includes such materials.

Cells are largely classified into two types, suspended cells and adherent cells, based on the feature of their living form. For culturing of adherent cells, a range is limited within a scaffold in which the cells grow during the course of their division and proliferation, and therefore with continued proliferation it is unavoidable that they eventually reach the limit of proliferation in the scaffold. This is a fact common to both culturing on flat surfaces such as standard plates, and three-dimensional culturing using a substrate.

Subculturing is absolutely indispensable to promote cell growth and is an important process regardless of the purpose and method, but the operations of treating the cells with trypsin or collagenase to remove them from the scaffold, and reseeding them via a cell suspension, not only run the risk of contamination but are also time consuming, while stress exerted on the cells is another factor that cannot be overlooked.

In microcarrier culturing, which may be considered a typical culturing method in which medium is employed, it has been possible to achieve exchanging the cells between the carriers, but since their handling is carried out by microcarrier culturing, the method is still limited by the form of the microcarrier and subject to restrictions on the shape and size of the microcarrier.

In recent years, inventions by Kyoto University, Nissan Chemical Industries, Ltd. and Nipro Corp. relating to microcarrier culturing have provided methods for mass culturing of ES and iPS cells using gellan gum, and methods for subculturing of cells without cell suspensions have been discovered. Such methods are carried out while suspending formed cell cluster (called "spheroids") in liquid, wherein repeated enlargement and division of the spheroids allows the cell culturing to be achieved without suspension, but because these are limited to spheroid-forming cells, while many time consuming aspects are also involved including detailed timing control required to prevent aggregation of the spheroids, such methods are not very efficient and the morphological restrictions associated with microcarrier culturing still essentially have not been solved.

For common culturing methods, on the other hand, there is known a methodology in which a portion of the culturing surface of the cultured cells is covered using a removable rubber material, which is removed each time the cells are transferred and transported to a plate or the like for culturing, but while this essentially allows them to be temporarily transportable, from the viewpoint of expanding the method for continuous mass cell culturing, the aforementioned issues have not been dealt with and remain unsolved.

In order to culture and grow cells in mass quantities and efficiently prepare them for the intended purpose, it is desirable to subculture the cells using a highly adaptable system suited for convenience and automation in a manner without using a cell suspension, regardless of their form or sizes. In addition, it is a highly desirable goal to establish a novel system whereby the methodology can be directly implemented in constant cell culturing.

Porous Polyimide Film

The term "polyimide" is a general term for polymers including imide bonds in the repeating unit. An "aromatic polyimide" is a polymer in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

Porous polyimide films have been utilized in the prior art for filters and low permittivity films, and especially for battery-related purposes, such as fuel cell electrolyte membranes and the like. PTLs 8 to 10 describe porous polyimide films with numerous macro-voids, having excellent permeability for gases and the like, high porosity, excellent smoothness on both surfaces, relatively high strength and, despite high porosity, also excellent resistance against compression stress in the film thickness direction. All of these are porous polyimide films formed via amic acid.

CITATION LIST

Patent Literature

[PTL 1] Japanese Patent No. 5549209
[PTL 2] Japanese Patent No. 5460241
[PTL 3] WO2005/121311
[PTL 4] Japanese Unexamined Patent Publication No. 2001-190270
[PTL 5] Japanese Unexamined Patent Publication HEI No. 7-313151
[PTL 6] Japanese Unexamined Patent Publication HEI No. 5-335368
[PTL 7] Japanese Unexamined Patent Publication No. 2003-180337
[PTL 8] WO2010/038873
[PTL 9] Japanese Unexamined Patent Publication No. 2011-219585
[PTL 10] Japanese Unexamined Patent Publication No. 2011-219586

Non-Patent Literature

[NPL 1] Kurosawa, H., Seibutsu Kougaku, Vol. 91, 2013, No. 11, 646-653
[NPL 2] Otsuji et al., Stem Cell Reports, Vol. 2, 734-745, May 6, 2014

DISCLOSURE OF THE INVENTION

Problems to be Solved by the Invention

It is an object of the present invention to provide a cell culturing method and kit. More specifically, it is an object of the invention to provide a method and kit whereby cells are cultured on a support exposed to air.

Means for Solving the Problems

The present inventors have found that a sheet-like cell culture support such as a porous polyimide film is suitable for adhesion and culturing of cells, and have thereupon completed this invention. The present inventors have found that, by culturing cells on a sheet-like cell culture support such as a porous polyimide film and directly contacting it with a gas phase, it is possible to culture numerous cells in an extremely small volume, and have also verified the range of applicability of the method. While a major improvement in oxygen supply efficiency may be expected by directly contacting a support with a gas phase, since cell death is assumed to occur due to depletion of the medium we verified that the method is possible under various different conditions, and as a result we succeeded in completing the present invention. Furthermore, it was found that exposure of a support to a gas phase can improve adhesiveness between films and allow free movement of cells between the sheets, so that a desirably large three-dimensional space may be expected to be provided for the cells.

In addition, as a result of diligent research conducted with the aim of solving the problem of providing a method of subculturing cells by a highly adaptable system in a manner without a cell suspension, the present inventors found that desirable results can be obtained by cell culturing using a porous polyimide film, and have thereupon devised this invention. Specifically, in cell culturing using porous polyimide films, large-diameter communicating pores that allow passage of cells in the films are utilized to allow stable growth of the cells in the spaces so that, so long as the films are adhered to each other, the cells can migrate with some degree of freedom not only within the films but also across films. By utilizing this feature, and closely contacting a porous polyimide film in which the cells are not growing to medium in which the cells are growing (a plate, dish, culture plate, microcarrier, silica porous bodies, cellulose sponge, porous polyimide film or other cell culturing medium), migration of the cells is promoted, and cell culturing and subculturing can be continued in a continuous and convenient manner.

The present invention preferably includes, but is not limited to, the following modes.

[1]
A cell culturing method including:
(1) a step of supporting cells on one or more sheet-like porous supports,
(2) a step of applying a medium to the sheet-like porous support supporting the cells and wetting the sheet-like porous support with the medium, with the medium included in some or all of the pores of the sheet-like porous support,
(3) a step of disposing the sheet-like porous support in a culturing vessel that houses medium, in such a manner that all or a portion of the surface of the sheet-like porous support wetted with the medium is exposed to a gas phase, and
(4) a step of setting the culturing vessel in an incubator and culturing the cells, wherein the wetted state of the sheet-like porous support surface and interior is maintained throughout the culturing.

[2]
A culturing method according to [1], wherein in step (4), the medium is supplied into the culturing vessel in a continuous or intermittent manner, and all or a portion of the sheet-like porous support wetted with the medium is exposed to a gas phase throughout the culturing.

[3]
A method according to [1] or [2], wherein in step (4), the step of culturing the cells is a step of culturing while supplying oxygen by oxygen-supplying means.

[4]
A method according to any one of [1] to [3], wherein in step (3), the sheet-like porous support is mounted on a rigid body.

[5]
A method according to [4], wherein the rigid body is a metal mesh.

[6]
A method according to any one of [1] to [5], wherein in step (3), a porous sheet with a larger mean pore size than the sheet-like porous supports is mounted in such a manner as to cover all or a portion of the top surface of the one or more sheet-like porous support.

[7]
A method according to [6], wherein the porous sheet with a larger mean pore size than the sheet-like porous support is selected from the group consisting of nonwoven fabrics, gauzes and sponges.

[8]

A method according to any one of [1] to [7], wherein the culturing vessel is an open vessel.

[9]

A method according to any one of [1] to [7], wherein the culturing vessel is a closed vessel.

[10]

A method according to any one of [1] to [9], wherein in step (3), two or more sheet-like porous supports are disposed in a manner layered one over the other.

[11]

A method according to any one of [1] to [10], wherein in step (3), one or more sheet-like porous supports are disposed in a folded manner.

[12]

A method according to any one of [1] to [11], wherein the one or more sheet-like porous supports are porous polyimide films.

[13]

A method according to [12], wherein the porous polyimide film is a porous polyimide film including a polyimide obtained from a tetracarboxylic dianhydride and a diamine.

[14]

A method according to [13], wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[15]

A method according to [13] or [14], wherein the porous polyimide film is a porous polyimide film with a multilayer structure, having two different surface layers and a macrovoid layer.

[16]

A method according to any one of [1] to [15], wherein the cells are transformed by genetic engineering technology so as to express a substance.

[17]

A method according to any one of [1] to [16], wherein the cells are selected from the group consisting of animal cells, insect cells, plant cells, yeast cells and bacteria.

[18]

A method according to [17], wherein the animal cells are cells derived from an animal belonging to the subphylum Vertebrata.

[19]

A method according to [18], wherein the cells are selected from the group consisting of CHO cells, CHO-K1 cells, Vero cells and MDCK cells.

[20]

A kit for use in the method according to any one of [1] to [19], including a porous polyimide film.

[21]

The use of a porous polyimide film for the method according to any one of [1] to [19].

[22]

A method of culturing cells by allowing them to migrate onto a porous polyimide film, the method including contacting a porous polyimide film with a cell culture substrate in which cells are being cultured to allow the cells to migrate from the cell culture substrate onto the porous polyimide film, and culturing the cells that have been allowed to migrate onto the porous polyimide film.

[23]

A method according to [22], wherein the cell culture substrate is selected from the group consisting of plates, dishes, culture plates, culture flasks, microwell plates and glass bottom dishes, and the porous polyimide film is contacted with the top surface of the cell culture substrate.

[24]

A method according to [22], wherein the cell culture substrate is selected from the group consisting of microcarriers, silica porous bodies, cellulose sponges, nonwoven fabrics and hollow fibers, and one or more porous polyimide films are contacted with the cell culture substrate from the top, bottom or both.

[25]

A method of culturing cells by allowing them to migrate onto a porous polyimide film, the method including contacting the top surface or bottom surface, or both, of a first porous polyimide film on which cells are being cultured, with a second porous polyimide film on which cells are not being cultured, to allow the cells to migrate from the first porous polyimide film to the second porous film, and culturing the cells that have been allowed to migrate to the second porous polyimide film.

[26]

A method according to [25] wherein, while the first porous polyimide film and the second porous polyimide film are in a contacted state, the film aggregate is lifted up into a gas phase.

[27]

A method according to [25] or [26], further including a step in which cells are applied to the empty first porous polyimide film wherein cells are not being cultured, and the cells are cultured on the first porous polyimide film.

[28]

A method according to [27], wherein the empty first porous polyimide film is contacted with the cell culture substrate in which cells are being cultured, and the cells are allowed to migrate from the cell culture substrate to the porous polyimide film to apply the cells to the first porous polyimide film.

[29]

A method of culturing cells by allowing them to migrate onto a porous polyimide film, the method including contacting a cell-containing biological sample with the top surface or bottom surface, or both, of a porous polyimide film, to allow the cells to migrate from the biological sample to the porous polyimide film, and culturing the cells that have been allowed to migrate to the porous polyimide film.

[30]

A method according to any one of [22] to [29], wherein the porous polyimide film is a porous polyimide film including a polyimide obtained from a tetracarboxylic dianhydride and a diamine.

[31]

A method according to [30], wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[32]

A method according to [30] or [31], wherein the porous polyimide film is a porous polyimide film with a multilayer structure, having two different surface layers and a macrovoid layer.

[33]

A method according to [32], wherein the film thickness of the porous polyimide film is no greater than 75 μm.

[34]
A method according to any one of [22] to [33], wherein two or more porous polyimide films to which the cells have migrated are layered either above and below or left and right in the cell culture medium, and the cells are cultured.

[35]
A method according to any one of [22] to [34], which includes repeating two or more times the procedure of allowing the cells to migrate from the cell culture substrate in which cells are being cultured, the cell-containing biological sample or the porous polyimide film in which cells are being cultured, to the porous polyimide film in which cells are not being cultured.

[36]
A kit for use in a method according to any one of [22] to [35], including a porous polyimide film.

[37]
The use of a porous polyimide film for the method according to any one of [22] to [35].

Effect of the Invention

The present invention allows air to be efficiently supplied to cells, by culturing the cells using a sheet-like porous support such as a porous polyimide film, during which time a wet environment is maintained on the sheet-like porous support interior and surface while all or a portion of the sheet-like porous support surface is exposed to a gas phase. According to the invention there is no need for a special apparatus for oxygen supply, even in a large-scale cell culture system. Moreover, according to the invention, the sheet-like porous support is not settled deep inside the medium and hence there is not necessarily any need to move the sheet-like porous support for medium exchange. For example, medium exchange can be accomplished by creating a continuous or intermittent flow of the medium on the top or the bottom of the sheet-like porous support. In addition, since there is no need for movable parts for stirring or the like in the cell culture system employing the method of the invention, it is possible to provide a robust, highly stable cell culture system.

Moreover, by using a porous polyimide film by the method of the invention, it has become possible to conveniently and efficiently subculture cells in a manner without a cell suspension.

In addition, even when cells have reached confluency which is necessary for subculturing of conventional adherent cells, according to the invention a porous polyimide film having a space in which the cells are not seeded and/or where the cells can adhere may be attached (for example, by clamping or layering) onto a cell culture support that has become confluent or subconfluent, to allow expanded culturing without using trypsin or the like that is used in the prior art.

BRIEF DESCRIPTION OF THE DRAWINGS

FIG. 15 is a graph showing the results of culturing human skin fibroblasts by the method of the invention.

MODE FOR CARRYING OUT THE INVENTION

I. Cell Culturing Method

Figure 1:
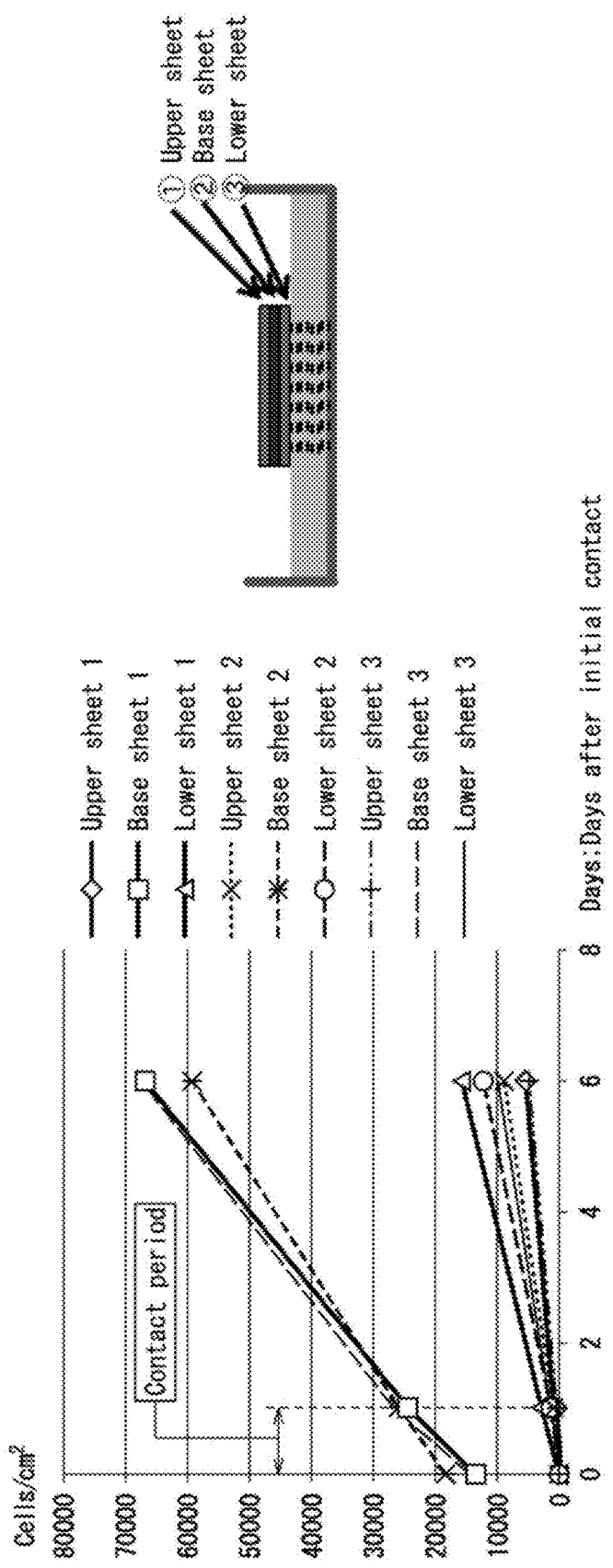
FIG. 1 shows the results of examining migration of cells in Example 3, when a porous polyimide film in which cells are being cultured is sandwiched in close contact with one upper and lower empty porous polyimide film each, and their aggregate is exposed to a gas phase.

The present invention relates to a cell culturing method. The entire content of International Application Number PCT/JP2014/070407 is incorporated herein by reference.

The cell culturing method of the invention includes supporting and culturing cells on a sheet-like porous support such as a porous polyimide film. The present inventors have found that a sheet-like porous support is suitable for adhesion and culturing of cells, and have thereupon completed this invention. The method of the invention includes applying cells to a sheet-like porous support and culturing the cells on the surface or in the interior of the polyimide film.

1. Sheet-Like Porous Support

The sheet-like porous support used for the invention may be any one that is a sheet-like support having pores that can hold cells, and examples include nonwoven fabrics, polymeric porous films and porous polyimide films. A porous polyimide film may be most preferably used. Naturally, a sheet-like porous support such as a porous polyimide film for supporting cells according to the invention is preferably in a state including no cells other than those that are to be loaded, i.e. in a sterilized state. The method of the invention preferably includes a step of pre-sterilizing the sheet-like porous support, such as a porous polyimide film. A porous polyimide film has very excellent heat resistance and is lightweight, allows free selection of the shape and size, and is easy to treat for sterilization. Any desired sterilization treatment may be conducted, such as dry air sterilization, steam sterilization, sterilization with a disinfectant such as ethanol, or electromagnetic wave sterilization using ultraviolet rays or gamma rays.

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

The porous polyimide film used for the invention is preferably a porous polyimide film including (as the main component) a polyimide obtained from a tetracarboxylic dianhydride and a diamine, and more preferably it is a porous polyimide film comprising a polyimide obtained from a tetracarboxylic dianhydride and a diamine. The phrase "including as the main component" means that it essentially contains no components other than the polyimide obtained from a tetracarboxylic dianhydride and a diamine, as constituent components of the porous polyimide film, or that it may contain them but they are additional components that do not affect the properties of the polyimide obtained from the tetracarboxylic dianhydride and diamine.

This also includes colored porous polyimide films obtained by forming a polyamic acid solution composition containing a polyamic acid solution obtained from a tetracarboxylic acid component and a diamine component, and a coloring precursor, and then heat treating it at 250° C. or higher.

Polyamic Acid

A polyamic acid is obtained by polymerization of a tetracarboxylic acid component and a diamine component. A polyamic acid is a polyimide precursor that can be cyclized to a polyimide by thermal imidization or chemical imidization.

The polyamic acid used may be any one that does not have an effect on the invention, even if a portion of the amic acid is imidized. Specifically, the polyamic acid may be partially thermally imidized or chemically imidized.

When the polyamic acid is to be thermally imidized, there may be added to the polyamic acid solution, if necessary, an imidization catalyst, an organic phosphorus-containing compound, or fine particles such as inorganic fine particles or organic fine particles. Also, when the polyamic acid is to be chemically imidized, there may be added to the polyamic acid solution, if necessary, a chemical imidization agent, a dehydrating agent, or fine particles such as inorganic fine particles or organic fine particles. Even if such components are added to the polyamic acid solution, they are preferably added under conditions that do not cause precipitation of the coloring precursor.

Coloring Precursor

For the purpose of the invention, a coloring precursor is a precursor that generates a colored substance by partial or total carbonization under heat treatment at 250° C. or higher.

Coloring precursors to be used for the invention are preferably uniformly dissolved or dispersed in a polyamic acid solution or polyimide solution and subjected to thermal decomposition by heat treatment at 250° C. or higher, preferably 260° C. or higher, even more preferably 280° C. or higher and more preferably 300° C. or higher, and preferably heat treatment in the presence of oxygen such as air, at 250° C. or higher, preferably 260° C. or higher, even more preferably 280° C. or higher and more preferably 300° C. or higher, for carbonization to produce a colored substance, more preferably producing a black colored substance, with carbon-based coloring precursors being most preferred.

The coloring precursor, when being heated, first appears as a carbonized compound, but compositionally it contains other elements in addition to carbon, and also includes layered structures, aromatic crosslinked structures and tetrahedron carbon-containing disordered structures.

Carbon-based coloring precursors are not particularly restricted, and for example, they include tar or pitch such as petroleum tar, petroleum pitch, coal tar and coal pitch, coke, polymers obtained from acrylonitrile-containing monomers, ferrocene compounds (ferrocene and ferrocene derivatives), and the like. Of these, polymers obtained from acrylonitrile-containing monomers and/or ferrocene compounds are preferred, with polyacrylnitrile being preferred as a polymer obtained from an acrylonitrile-containing monomer.

The tetracarboxylic dianhydride used may be any tetracarboxylic dianhydride, selected as appropriate according to the properties desired. Specific examples of tetracarboxylic dianhydrides include biphenyltetracarboxylic dianhydrides such as pyromellitic dianhydride, 3,3',4,4'-biphenyltetracarboxylic dianhydride (s-BPDA) and 2,3,3',4'-biphenyltetracarboxylic dianhydride (a-BPDA), oxydiphthalic dianhydride, diphenylsulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride, 2,3,3',4'-benzophenonetetracarboxylic dianhydride, 3,3',4,4'-benzophenonetetracarboxylic dianhydride, bis(3,4-dicarboxyphenyl)methane dianhydride, 2,2-bis(3,4-dicarboxyphenyl)propane dianhydride, p-phenylenebis(trimellitic acid monoester acid anhydride), p-biphenylenebis (trimellitic acid monoester acid anhydride), m-terphenyl-3,4,3',4'-tetracarboxylic dianhydride, p-terphenyl-3,4,3',4'-tetracarboxylic dianhydride, 1,3-bis(3,4-dicarboxyphenoxy) benzene dianhydride, 1,4-bis(3,4-dicarboxyphenoxy) benzene dianhydride, 1,4-bis(3,4-dicarboxyphenoxy) biphenyl dianhydride, 2,2-bis[(3,4-dicarboxyphenoxy) phenyl]propane dianhydride, 2,3,6,7-naphthalenetetracarboxylic dianhydride, 1,4,5,8-naphthalenetetracarboxylic dianhydride, 4,4'-(2,2-hexafluoroisopropylidene)diphthalic dianhydride, and the like. Also preferably used is an aromatic tetracarboxylic acid such as 2,3,3',4'-diphenylsulfonetetracarboxylic acid. These may be used alone or in appropriate combinations of two or more.

Particularly preferred among these are at least one type of aromatic tetracarboxylic dianhydride selected from the group consisting of biphenyltetracarboxylic dianhydride and pyromellitic dianhydride. As a biphenyltetracarboxylic dianhydride there may be suitably used 3,3',4,4'-biphenyltetracarboxylic dianhydride.

Any desired diamine may be used as a diamine. Specific examples of diamines include the following.
1) Benzenediamines with one benzene nucleus, such as 1,4-diaminobenzene(paraphenylenediamine), 1,3-diaminobenzene, 2,4-diaminotoluene and 2,6-diaminotoluene;
2) diamines with two benzene nuclei, including diaminodiphenyl ethers such as 4,4'-diaminodiphenyl ether and 3,4'-diaminodiphenyl ether, and 4,4'-diaminodiphenylmethane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenylmethane, 3,3'-dicarboxy-4,4'-diaminodiphenylmethane, 3,3',5,5'-tetramethyl-4,4'-diaminodiphenylmethane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenylsulfone, 3,4'-diaminodiphenylsulfone, 4,4'-diaminodiphenylsulfone, 3,3'-diaminobenzophenone, 3,3'-diamino-4,4'-dichlorobenzophenone, 3,3'-diamino-4,4'-dimethoxybenzophenone, 3,3'-diaminodiphenylmethane, 3,4'-diaminodiphenylmethane, 4,4'-diaminodiphenylmethane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide and 4,4'-diaminodiphenyl sulfoxide;
3) diamines with three benzene nuclei, including 1,3-bis(3-aminophenyl)benzene, 1,3-bis(4-aminophenyl)benzene, 1,4-bis(3-aminophenyl)benzene, 1,4-bis(4-aminophenyl) benzene, 1,3-bis(4-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy)benzophenone, 1,3-bis(3-aminophenyl sulfide)benzene, 1,3-bis(4-aminophenyl sulfide)benzene, 1,4-bis(4-aminophenyl sulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl)isopropyl]benzene, 1,4-bis[2-(3-aminophenyl)isopropyl]benzene and 1,4-bis[2-(4-aminophenyl) isopropyl]benzene;

4) diamines with four benzene nuclei, including 3,3'-bis(3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy)phenyl]ether, bis[3-(4-aminophenoxy)phenyl]ether, bis[4-(3-aminophenoxy)phenyl]ether, bis[4-(4-aminophenoxy)phenyl]ether, bis[3-(3-aminophenoxy)phenyl]ketone, bis[3-(4-aminophenoxy)phenyl]ketone, bis[4-(3-aminophenoxy)phenyl]ketone, bis[4-(4-aminophenoxy)phenyl]ketone, bis[3-(3-aminophenoxy)phenyl] sulfide, bis[3-(4-aminophenoxy)phenyl] sulfide, bis[4-(3-aminophenoxy)phenyl] sulfide, bis[4-(4-aminophenoxy)phenyl] sulfide, bis[3-(3-aminophenoxy)phenyl]sulfone, bis[3-(4-aminophenoxy)phenyl]sulfone, bis[4-(3-aminophenoxy)phenyl]sulfone, bis[4-(4-aminophenoxy)phenyl]sulfone, bis[3-(3-aminophenoxy)phenyl]methane, bis[3-(4-aminophenoxy)phenyl]methane, bis[4-(3-aminophenoxy)phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy)phenyl]propane, 2,2-bis[4-(4-aminophenoxy)phenyl]propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy)phenyl]-1,1,1,3,3,3-hexafluoropropane and 2,2-bis[4-(4-aminophenoxy) phenyl]-1,1,1,3,3,3-hexafluoropropane.

These may be used alone or in mixtures of two or more. The diamine used may be appropriately selected according to the properties desired.

Preferred among these are aromatic diamine compounds, with 3,3'-diaminodiphenyl ether, 3,4'-diaminodiphenyl ether, 4,4'-diaminodiphenyl ether, paraphenylenediamine, 1,3-bis(3-aminophenyl)benzene, 1,3-bis(4-aminophenyl) benzene, 1,4-bis(3-aminophenyl)benzene, 1,4-bis(4-aminophenyl)benzene, 1,3-bis(4-aminophenoxy)benzene and 1,4-bis(3-aminophenoxy)benzene being preferred for use. Particularly preferred is at least one type of diamine selected from the group consisting of benzenediamines, diaminodiphenyl ethers and bis(aminophenoxy)phenyl.

From the viewpoint of heat resistance and dimensional stability under high temperature, the porous polyimide film is preferably formed from a polyimide obtained by combination of a tetracarboxylic dianhydride and a diamine, having a glass transition temperature of 240° C. or higher, or without a distinct transition point at 300° C. or higher.

From the viewpoint of heat resistance and dimensional stability under high temperature, the porous polyimide film of the invention is preferably a porous polyimide film comprising one of the following aromatic polyimides.
(i) An aromatic polyimide comprising at least one tetracarboxylic acid unit selected from the group consisting of biphenyltetracarboxylic acid units and pyromellitic acid units, and an aromatic diamine unit,
(ii) an aromatic polyimide comprising a tetracarboxylic acid unit and at least one type of aromatic diamine unit selected from the group consisting of benzenediamine units, diaminodiphenyl ether units and bis(aminophenoxy)phenyl units, and/or,
(iii) an aromatic polyimide comprising at least one type of tetracarboxylic acid unit selected from the group consisting of biphenyltetracarboxylic acid units and pyromellitic acid units, and at least one type of aromatic diamine unit selected from the group consisting of benzenediamine units, diaminodiphenyl ether units and bis(aminophenoxy)phenyl units.

While not restrictive, the porous polyimide film for use in the method of the invention may be a porous polyimide film with a multilayer structure, having at least two surface layers (A-surface and B-surface), and a macro-void layer sandwiched between the two surface layers. Preferably, the porous polyimide film is a porous polyimide film wherein the macro-void layer has a partition bonded to the surface layers (A-surface and B-surface) and a plurality of macro-voids with mean pore sizes of 10 to 500 μm in the planar direction of the film, surrounded by the partition and the surface layers (A-surface and B-surface), wherein the macro-void layer partition and the surface layers (A-surface and B-surface) each have thicknesses of 0.01 to 20 μm, with a plurality of pores with mean pore sizes of 0.01 to 100 μm, the pores being optionally communicating with each other, and also having a partial or total multilayer structure in communication with the macro-voids, where the total film thickness is 5 to 500 μm and the porosity is 40% or greater and less than 95%.

The total film thickness of the porous polyimide film used for the invention is not limited, but may be 20 to 75 μm according to one mode. Differences in the film thickness may be observed as differences in cell growth rate, cell morphology, cell saturation within the plate, and the like.

According to the invention, when the porous polyimide film used has two different surface layers (A-surface and B-surface), and a macro-void layer sandwiched between the two surface layers, the mean pore size of the holes in the A-surface may differ from the mean pore size of the holes in the B-surface. Preferably, the mean pore size of the holes in the A-surface is smaller than the mean pore size of the holes in the B-surface. More preferably, the mean pore size of the holes in the A-surface is smaller than the mean pore size of the holes in the B-surface, with the mean pore size of the holes in the A-surface being 0.01 to 50 μm, 0.01 μm to 40 μm, 0.01 μm to 30 μm, 0.01 μm to 20 μm or 0.01 μm to 15 μm, and the mean pore size of the holes in the B-surface being 20 μm to 100 μm, 30 μm to 100 μm, 40 μm to 100 μm, 50 μm to 100 μm or 60 μm to 100 μm. Most preferably, the A-surface of the porous polyimide film is a mesh structure having small holes with a mean pore size of no greater than 15 μm, such as 0.01 μm to 15 μm, and the B-surface is a large-hole structure with a mean pore size of 20 μm or greater, such as 20 μm to 100 μm.

The total film thickness of the porous polyimide film used for the invention can be measured using a contact thickness gauge.

The mean pore size of the surface of the porous polyimide film can be determined by measuring the pore area of 200 or more open holes from a scanning electron micrograph of the porous film surface, and calculating the mean diameter from the average value for the pore areas according to the following formula (1), assuming the pore shapes to be circular.

$$\text{Mean pore size} = 2 \times \sqrt{(Sa/\pi)} \tag{1}$$

(wherein Sa represents the average value for the pore areas)

The porosity of the porous polyimide film used for the invention can be determined by measuring the film thickness and mass of the porous film cut out to a prescribed size, and performing calculation from the basis weight according to the following formula (2).

$$\text{Porosity (\%)} = (1 - w/(S \times d \times D)) \times 100 \tag{2}$$

(wherein S represents the area of the porous film, d represents the total film thickness, w represents the measured mass, and D represents the polyimide density, the polyimide density being defined as 1.34 g/cm$^3$.)

For example, the porous polyimide films described in International Patent Publication No. WO2010/038873, Japanese Unexamined Patent Publication No. 2011-219585 and Japanese Unexamined Patent Publication No. 2011-219586 may also be used for the invention.

The cells that have been seeded on the surface of the porous polyimide film can stably grow and proliferate on the surface and/or in the interior of the film. The cells may be in a variety of different forms, depending on the location of growth and proliferation in the film. According to one mode of the invention, growth may be carried out while moving the surface and interior of the porous polyimide film and changing the form, depending on the type of cell.

2. Supporting of Cells on Sheet-Like Porous Support

Throughout the present specification, supporting of cells on a sheet-like porous support means that cells are held on all or a portion of either the surface or interior, or both the surface and interior, of a sheet-like porous support. The specific step for supporting the cells on the sheet-like porous support is not particularly restricted. It is possible to carry out the steps described throughout the present specification, or to employ any desired method suited for applying cells to a film-like support. While not a restriction, when a porous polyimide film is used as the sheet-like porous support for the method of the invention, application of the cells to the porous polyimide film may include the following modes, for example.

(A) A mode including a step of seeding cells on the surface of a porous polyimide film;

(B) A mode including a step of:

placing a cell suspension on the dried surface of the porous polyimide film, allowing it to stand, or moving the porous polyimide film to promote efflux of the liquid, or stimulating part of the surface to cause absorption of the cell suspension into the film, and retaining the cells in the cell suspension inside the film and allowing the water to flow out; and (C) A mode including a step of:

wetting one or both sides of the porous polyimide film with a cell culture solution or a sterilized liquid, loading a cell suspension into the wetted porous polyimide film, and retaining the cells in the cell suspension inside the film and allowing the water to flow out.

Mode (A) includes a step of directly seeding cells or a cell mass on the surface of a porous polyimide film. Alternatively, it includes a mode of placing a porous polyimide film in a cell suspension and wetting the cell culture solution from the surface of the film.

Cells seeded on the surface of a porous polyimide film adhere to the porous polyimide film and infiltrate into the interiors of the pores. Preferably, the cells adhere spontaneously to the porous polyimide film without applying any particular exterior physical or chemical force. The cells that have been seeded on the surface of the porous polyimide film can stably grow and proliferate on the surface and/or in the interior of the film. The cells may be in a variety of different forms, depending on the location of the film used for growth and proliferation.

For mode (B), a cell suspension is placed on the dried surface of a porous polyimide film. The porous polyimide film is allowed to stand, or the porous polyimide film is moved to promote efflux of the liquid, or part of the surface is stimulated to cause absorption of the cell suspension into the film, so that the cell suspension permeates into the film. While it is not our intention to be constrained by theory, this is believed to be due to the properties of each of the surface forms of the porous polyimide film. According to this mode, the cells are absorbed and seeded in the locations of the film where the cell suspension has been loaded.

Alternatively, as according to mode (C), after all or a portion of one or both sides of the porous polyimide film has been wetted with the cell culture solution or sterilized liquid, the cell suspension may be loaded into the wetted porous polyimide film. This will significantly increase the transit rate of the cell suspension.

For example, a method of wetting a portion of the film edges, for the main purpose of preventing fly loss of the film, may be used (hereunder referred to as "single-point wetting method"). The single-point wetting method is nearly the same as the dry method (mode (B)) in which the film essentially is not wetted. However, it is possible that cell solution permeation through the film is more rapid at the small wetted portions. There may also be used a method in which all of one or both sides of the porous polyimide film that have been thoroughly wetted (hereunder this will also be referred to as "wet film") is loaded with a cell suspension (this will hereunder be referred to as "wet film method"). In this case, the entire porous polyimide film has a greatly increased transit rate for the cell suspension.

According to modes (B) and (C), the cells in the cell suspension are retained in the film, while the water flows out. This allows treatment such as increasing the concentration of cells in the cell suspension and flowing out of unwanted non-cellular components together with the water.

Mode (A) will also be referred to as "natural seeding", and modes (B) and (C) as "suction seeding".

Preferably, but not restrictively, the viable cells are selectively retained in the porous polyimide film. Thus, according to a preferred mode of the invention, the viable cells are retained in the porous polyimide film, and the dead cells preferentially flow out together with the water.

The sterilized liquid used for mode (C) is not particularly restricted, and may be a sterilized buffering solution or sterilized water. A buffering solution may be, for example, (+) or (−) Dulbecco's PBS, or (+) or (−) Hank's Balanced Salt Solution. Examples of buffering solutions are listed in Table 1 below.

TABLE 1

| Component | Concentration (mmol/L) | Concentration (g/L) |
| --- | --- | --- |
| NaCl | 137 | 8.00 |
| KCl | 2.7 | 0.20 |
| $Na_2HPO_4$ | 10 | 1.44 |
| $KH_2PO_4$ | 1.76 | 0.24 |
| pH (−) | 7.4 | 7.4 |

In the method of the invention, application of cells to the porous polyimide film further includes a mode of adding adherent cells in a floating state as a suspension together with the porous polyimide film, to adhere the cells with the film (entangling). For example, for application of the cells to the porous polyimide film in the cell culturing method of the invention, the cell culture medium, the cells and one or more of the porous polyimide films may be placed in the cell culturing vessel. When the cell culture medium is a liquid, the porous polyimide film is in a floating state in the cell culture medium. The cells can adhere to the porous polyimide film due to the properties of the porous polyimide film. Thus, even with cells that are not suited for natural suspension culture, the porous polyimide film allows culturing in a floating state in the cell culture medium. The cells preferably spontaneously adhere to the porous polyimide film. Here, "adhere spontaneously" means that the cells are retained on the surface or in the interior of the porous polyimide film without applying any particular exterior physical or chemical force.

For example, the aforementioned method allows cells to be supported on a sheet-like porous support.

3. Wetting of Sheet-Like Porous Support with Medium

The method of the invention includes a step of applying medium to a sheet-like porous support on which cells have been supported, and wetting the sheet-like porous support with the medium in a manner in which the medium is contained in all or some of the pores of the sheet-like porous support.

Throughout the present specification, a state in which the sheet-like porous support is wetted with medium is a state in which the medium is contained in all or some of the pores on the surface or in the interior of the sheet-like porous support.

The method of wetting the sheet-like porous support with the medium may be any method that allows the medium to be applied to the sheet-like porous support in a state with the medium contained in all or some of the pores on the surface or in the interior of the sheet-like porous support. For example, the sheet-like porous support may be wetted with the medium simultaneously when the cells are supported on the sheet-like porous support by the method described above. Alternatively, after the cells have been supported on the sheet-like porous support using a medium-free solution, the medium may be applied onto the sheet-like porous support to exchange the solution in the sheet-like porous support with the medium. A medium in droplet form may also be applied by spraying onto the sheet-like porous support.

4. Exposure of Sheet-Like Porous Support to Gas Phase (First Mode)

The method of the invention includes a step of disposing a sheet-like porous support in a culturing vessel that houses a medium, in such a manner that all or a portion of the surface of the sheet-like porous support that has been wetted with the medium is exposed to a gas phase. Normally, when cells are cultured at high density or when cells which require a lot of oxygen are cultured, the oxygen consumption increases in a manner dependent on the cell count, thereby reducing the dissolved oxygen content of the medium, and this has complicated efforts to carry out culturing in environments with increased cell density. When cell culturing is carried out at high density, therefore, it has been necessary to separately provide a controller to increase the oxygen content in the medium. However, since the method of the invention allows oxygen in a gas phase to be directly supplied to the sheet-like porous support, there is no need for a special apparatus to supply oxygen to the medium, and a limitless supply of oxygen can be provided to the cells during culturing. Furthermore, since drying of the culture medium that commonly occurs upon exposure to a gas phase can be avoided due to the robust moisture retention property exhibited by the porosity of the porous polyimide film, culturing can be carried out while being exposed to a gas phase. Optionally, the invention may also further comprise means for supplying oxygen to the medium (for example, oxygen supply means by bubbling or the like, medium stirring means, etc.). The oxygen-supplying means may alternatively be provided inside the culturing vessel.

Moreover, by employing a step of disposing sheet-like porous supports in such a manner that all or portions of the surfaces of the sheet-like porous supports are exposed to a gas phase, as according to the invention, the sheet-like porous supports come into close contact at the portions where the sheet-like porous supports overlap, the space in which the cells are able to adhere being increased in proportion to the area (volume) of the sheet-like porous supports, and the space in which the sheet-like porous supports are held and culturing takes place can thereby be minimized. When a support such as a microcarrier is used for culturing in a conventional liquid medium, collision between the supports must be prevented in order to increase the number of cells cultured, and this necessarily requires the amount of medium to be increased, resulting in a larger space for holding of the support and culturing. In contrast, the present invention allows sheet-like porous supports to be disposed while being exposed to a gas phase, and thus provides advantages not found in the prior art, such as having the sheet-like porous supports in close contact and minimizing the culturing space. While the number of layers will of course be limited due to the need to supply oxygen and nutrients, since the sheets themselves are flexible, three-dimensional and very thin, it is possible to adequately and stably supply oxygen and nutrients by diffusion alone and thus achieve prolonged cell culturing in a stable manner even with long-term culturing using 30 or more layers, for example. In addition, exposure to gas phase improves the adhesion between the porous polyimide films in a very satisfactory manner, and the cells can freely move in and out between the sheets and, by a simple method of adding sheets, it is possible to obtain an essentially similar effect as subculturing by free dispersion of the cells into adjacent contacting empty sheets and proliferation.

The cell culture medium to be used in the method of the invention (this may be referred to simply as "medium" throughout the present specification) may be in any form such as a liquid medium, semi-solid medium or solid medium, but it is preferably used as a liquid medium. Also, a liquid medium in droplet form may be sprayed into the cell culturing vessel to contact the medium with the sheet-like porous support.

In the culturing method of the invention, two or more fragments of the sheet-like porous supports may also be used. In common culturing that does not employ a sheet-like porous support, the base area of the vessel constitutes the upper limit for the cell culturing area, but in cell culturing using sheet-like porous supports, the entire large surface area of the previously introduced sheet-like porous supports serves as the cell culturing area. A sheet-like porous support allows the cell culture solution to pass through, allowing supply of nutrients, oxygen and the like even into the folded film, for example.

The sizes and shapes of the sheet-like porous support fragments are not particularly restricted. The shapes may be as desired, such as circular, elliptical, quadrilateral, triangular, polygonal or string-like.

Various shapes of Sheet-like porous supports may also be used. Instead of a flat form, each sheet-like porous support can also be used by working into a three-dimensional shape. For example, sheet-like porous supports may be: i) folded, ii) wound into a roll, iii) connected as sheets or fragments by a filamentous structure, or iv) bound into a rope, for suspension or fixing in the cell culture medium in the cell culturing vessel. By forming into shapes such as i) to iv), it is possible to place a large number of sheet-like porous supports in a fixed volume of cell culture medium, similar to using fragments. Furthermore, since each fragment can be treated as an aggregate, it is possible to aggregate and move the cell masses together, for overall high applicability.

With the same concept as fragment aggregates, two or more sheet-like porous supports may be used in a layered form either above and below or left and right in the cell culture medium. Layering includes a mode where portions of the sheet-like porous supports overlap. Layered culturing allows culturing of cells at high density in a narrow space. It is also possible to further layer a film on the film on which cells are already growing, to create a multilayer of different cell types. There are no particular restrictions on the number of sheet-like porous supports layered.

Depending on the purpose, any desired method may be employed as the method of disposing the sheet-like porous supports in such a manner that all or portions of the medium-wetted sheet-like porous support surfaces are exposed to the gas phase.

For example, the medium may be removed from the sheet-like porous supports in which cells have been seeded or in which cells are being cultured in the cell culturing vessel, creating a state in which the medium is essentially absent from the exteriors of the sheet-like porous supports. In this case, a porous sheet with a larger mean pore size than the sheet-like porous supports may be mounted so as to cover all or portions of the top surfaces of the sheet-like porous supports. The porous sheet used may be any one so long as it has a larger mean pore size than the porous polyimide film, and for example, a nonwoven fabric, gauze or sponge may be suitably used. If a porous sheet with a larger mean pore size than a porous polyimide film is mounted on a porous polyimide film, drift current of medium, and especially liquid medium, flowing on the surface of the porous polyimide film can be minimized, allowing the medium to be homogeneously applied onto the surface of the porous polyimide film and thus increasing the culture efficiency.

Moreover, a rigid body such as a metal mesh may be set in the cell culturing vessel, and sheet-like porous supports in which cells have been seeded or in which cells are being cultured may be mounted on it so as to expose them to a gas phase. In this case as well, a porous sheet with a larger mean pore size than the sheet-like porous supports may be mounted so as to cover all or portions of the top surfaces of the sheet-like porous supports.

In addition, a cell culturing apparatus that allows the medium to be applied in a continuous or intermittent manner onto the sheet-like porous supports in which cells have been seeded or in which cells are being cultured may be used to create a condition where all or portions of the sheet-like porous supports are exposed to the gas phase. In this case as well, a porous sheet with a larger mean pore size than the sheet-like porous supports may be mounted so as to cover all or portions of the top surfaces of the sheet-like porous supports.

In the method of the invention, there are no particular restrictions on the form and scale of the system used for culturing. The culturing vessel used may be an open vessel or a closed vessel. For example, a cell-culturing dish, flask, plastic bag or test tube, or even a large-scale tank, may be used as appropriate. These include, for example, Cell Culture Dish by BD Falcon, and Nunc Cell Factory by Thermo Scientific.

The culturing in the method of the invention may be carried out in a manner with continuous circulation such as continuous addition and recovery of the medium on the porous polyimide film, or exposure of the porous polyimide film sheet to air using an open apparatus.

Cell culturing according to the invention may be carried out in a system in which a cell culture medium is continuously or intermittently supplied to a cell culturing vessel from cell culture medium supply means installed outside of the cell culturing vessel. The system may be such that the cell culture medium is circulated between the cell culture medium supply means and the cell culturing vessel.

When the cell culturing is to be carried out in a system in which the cell culture medium is continuously or intermittently supplied to the cell culturing vessel from cell culture medium supply means installed outside of the cell culturing vessel, the system may be a cell culturing apparatus including a culturing unit which is the cell culturing vessel, and a culture medium-supply unit which is the cell culture medium supply means, wherein the culturing unit is a culturing unit that houses one or more porous polyimide films to support cells, and that comprises a culture medium supply port and a culture medium discharge port, and the culture medium-supply unit is a culture medium-supply unit comprising a culture medium housing vessel, a culture medium supply line, and a liquid conveyance pump that conveys the medium continuously or intermittently through the culture medium supply line, the first end of the culture medium supply line contacting the medium in the culture medium housing vessel, and the second end of the culture medium supply line being in communication with the culturing unit interior via the culture medium supply port of the culturing unit.

The culturing unit in the cell culturing apparatus may be a culturing unit that does not comprise an air supply port, an air discharge port and an oxygen exchange membrane, or it may be a culturing unit that comprises an air supply port and an air discharge port, or an oxygen exchange membrane. Even if the culturing unit does not comprise an air supply port, and an air discharge port and an oxygen exchange membrane, the oxygen, etc. necessary for cell culturing will be adequately supplied to the cells through the medium. Furthermore, in the cell culturing apparatus described above, the culturing unit may further comprise a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.

5. Cell Culturing

In the method of the invention, a culturing vessel having sheet-like porous supports disposed therein in such a manner that all or portions of the surfaces of the sheet-like porous supports that have been wetted with medium are exposed to a gas phase, as described above, is set in an incubator and the cells are cultured.

The incubator used may be any one that can maintain a temperature suited for culturing of cells. An incubator that can adjust the humidity and $CO_2$ concentration, in addition to the temperature, may also be used. When using ordinary animal cells, an incubator that can supply 5% $CO_2$ to the cell culturing apparatus may be used.

In the method of the invention, all or portions of the surfaces of sheet-like porous supports that have been wetted with medium are exposed to a gas phase throughout culturing of the cells. In addition, the surfaces and interiors of the sheet-like porous supports are kept in a wetted state throughout culturing of the cells.

The method for keeping the surfaces and interiors of the sheet-like porous supports in a wetted state throughout culturing of the cells may be any desired method used as appropriate. For example, the sheet-like porous supports that have been wetted with the medium may be housed in a closed vessel to maintain high humidity inside the vessel. In this case, the humidity inside the vessel is preferably 50% or greater, 60% or greater, 70% or greater, 80% or greater, 90% or greater or 99% or greater. Also, as mentioned above, there may be used a cell culturing apparatus that allows the medium to be applied in a continuous or intermittent manner onto the sheet-like porous supports in which cells have been seeded or in which cells are being cultured, in order to maintain a wetted state on the surfaces and interiors of the sheet-like porous supports throughout the culturing.

6. Cells

There are no particular restrictions on the type of cells that can be utilized for the method of the invention, and it may be used for growth of any type of cells.

For example, the cells may be selected from the group consisting of animal cells, insect cells, plant cells, yeast cells and bacteria. Animal cells are largely divided into cells from animals belonging to the subphylum Vertebrata, and cells from non-vertebrates (animals other than animals belonging to the subphylum Vertebrata). There are no particular restrictions on the source of the animal cells, for the purpose of the present specification. Preferably, they are cells from an animal belonging to the subphylum Vertebrata. The subphylum Vertebrata includes the superclass Agnatha and the superclass Gnathostomata, the superclass Gnathostomata including the class Mammalia, the class Aves, the class Amphibia and the class Reptilia. Preferably, they are cells from an animal belonging to the class Mammalia, generally known as mammals. Mammals are not particularly restricted but include, preferably, mice, rats, humans, monkeys, pigs, dogs, sheep and goats.

There are also no particular restrictions on sources of plant cells, for the purpose of the present specification. Suitable cells are from plants including bryophytes, pteridophytes and spermatophytes.

Plants from which spermatophyte cells are derived include both monocotyledons and dicotyledons. While not restrictive, monocotyledons include Orchidaceae plants, Poaceae plants (rice, corn, barley, wheat, sorghum and the like) and Cyperaceae plants. Dicotyledons include plants belonging to many subclasses including the subclass Chrysanthemum, the subclass Magnoliidae and the subclass Rosidae.

Algae may be considered cell-derived organisms. These include different groups, from the eubacteria Cyanobacteria (blue-green algae), to eukaryotic monocellular organisms (diatoms, yellow-green algae, dinoflagellates and the like) and multicellular marine algae (red algae, brown algae and green algae).

There are no particular limitations on the types of archaebacteria or bacteria for the purpose of the present specification. Archaebacteria are composed of groups comprising methanogenic bacteria, extreme halophilic bacteria, thermophilic acidophilic bacteria, hyperthermophilic bacteria and the like. Bacteria are selected from the group consisting of, for example, lactic acid bacteria, *E. coli, Bacillus subtilis* and cyanobacteria.

The types of animal cells or plant cells that may be used for the method of the invention are not particularly restricted, but are preferably selected from the group consisting of pluripotent stem cells, tissue stem cells, somatic cells and germ cells.

The term "pluripotent stem cells", for the purpose of the invention, is intended as a comprehensive term for stem cells having the ability to differentiate into cells of a variety of tissues (pluripotent differentiating power). While not restrictive, pluripotent stem cells include embryonic stem cells (ES cells), induced pluripotent stem cells (iPS cells), embryonic germ cells (EG cells) and germ stem cells (GS cells). They are preferably ES cells or iPS cells. Particularly preferred are iPS cells, which are free of ethical problems, for example. The pluripotent stem cells used may be any publicly known ones, and for example, the pluripotent stem cells described in International Patent Publication No. WO2009/123349 (PCT/JP2009/057041) may be used.

The term "tissue stem cells" refers to stem cells that are cell lines capable of differentiation but only to limited specific tissues, though having the ability to differentiate into a variety of cell types (pluripotent differentiating power). For example, hematopoietic stem cells in the bone marrow are the source of blood cells, while neural stem cells differentiate into neurons. Additional types include hepatic stem cells from which the liver is formed and skin stem cells that form skin tissue. Preferably, the tissue stem cells are selected from among mesenchymal stem cells, hepatic stem cells, pancreatic stem cells, neural stem cells, skin stem cells and hematopoietic stem cells.

The term "somatic cells" refers to cells other than germ cells, among the cells composing a multicellular organism. In sexual reproduction these are not passed on to the next generation. Preferably, the somatic cells are selected from among hepatocytes, pancreatic cells, muscle cells, bone cells, osteoblasts, osteoclasts, chondrocytes, adipocytes, skin cells, fibroblasts, pancreatic cells, renal cells and lung cells, or blood cells such as lymphocytes, erythrocytes, leukocytes, monocytes, macrophages or megakaryocytes.

The term "germ cells" refers to cells having the role of passing on genetic information to the succeeding generation in reproduction. These include, for example, gametes for sexual reproduction, i.e. the ova, egg cells, sperm, sperm cells, and spores for asexual reproduction.

The cells may also be selected from the group consisting of sarcoma cells, established cell lines and transformants. The term "sarcoma" refers to cancer occurring in non-epithelial cell-derived connective tissue cells, such as the bone, cartilage, fat, muscle or blood, and includes soft tissue sarcomas, malignant bone tumors and the like. Sarcoma cells are cells derived from sarcoma. The term "established cell line" refers to cultured cells that are maintained in vitro for long periods and reach a stabilized character and can be semi-permanently subcultured. Cell lines derived from various tissues of various species including humans exist, such as PC12 cells (from rat adrenal medulla), CHO cells (from Chinese hamster ovary), HEK293 cells (from human embryonic kidney), HL-60 cells from (human leukocytes) and HeLa cells (from human cervical cancer), Vero cells (from African green monkey kidney epithelial cells), MDCK cells (from canine renal tubular epithelial cells) and HepG2 cells (human hepatic cancer-derived cell line). The term "transformants" refers to cells with an altered genetic nature by extracellularly introduced nucleic acid (DNA and the like). Suitable methods are known for transformation of animal cells, plant cells and bacteria.

II. Kit for Use in Cell Culturing Method

The present invention also relates to a kit for use in the cell culturing method, the kit including a sheet-like porous film, and especially a porous polyimide film.

The kit of the invention may include constituent elements necessary for cell culturing in addition to the porous polyimide film, as appropriate. This includes, for example, the cells to be applied to the porous polyimide film, the cell culture medium, the continuous culture medium-supply apparatus, the continuous culture medium-circulating apparatus, the scaffold or module for support of the cell sheets, the cell culturing apparatus, and the kit instruction manual.

While not restrictive, one mode includes a package containing either one or a plurality of sterilized porous polyimide films stored in a transparent pouch, in a form allowing their use for cell culturing, or a kit having a sterile liquid encapsulated together with a porous polyimide film in the same pouch, in the form of an integrated film/liquid allowing efficient suction seeding.

III. Use of Sheet-Like Porous Film for Cell Culturing Method

The invention also relates to the use of a sheet-like porous film, and especially a porous polyimide film, for a cell culturing method.

The invention relates to a method and kit for culturing of cells while allowing them to migrate onto a porous polyimide film, as well as the use of the same. The method of subculturing and culturing cells according to the invention includes contacting a new porous polyimide film in which cells are not growing, with cells growing on a substrate (a plate, dish, culture plate, microcarrier, silica porous bodies, cellulose sponge, porous polyimide film or other cell culturing medium), and allowing the cells on the substrate to migrate to the empty porous polyimide film for subculturing or culturing of the cells. The present inventors have found that a porous polyimide film is suitable for adhesion and culturing of cells, and have thereupon completed this invention. The method of the invention includes contacting a porous polyimide film with different types of substrate in which cells are already growing, to allow migration of the cells to the polyimide film and culturing the cells on its surface or interior. Since the porous polyimide film provides a large space in which proliferation of cells can take place, migration of the cells becomes essentially equivalent to subculturing, and highly efficient proliferation of cells can be carried out without treatment with trypsin or the like, thus increasing efficiency and reducing damage to the cells. In addition, it is expected that cells with excellent adhesion and motility can be preferentially isolated from among mixtures of different types of cells such as in biological tissue.

IV. Method of Culturing Cells by Allowing them to Migrate onto Porous Polyimide Film (Second Mode)

According to one mode of the invention, the method includes contacting a porous polyimide film with a cell culture substrate in which cells are being cultured to allow the cells to migrate from the cell culture substrate onto the porous polyimide film, and culturing the cells that have been allowed to migrate onto the porous polyimide film. The cells migrate from the cell culture substrate in which the cells are being cultured, to a porous polyimide film.

1. Cells

The types of cells to be utilized in the method of the invention are not particularly restricted, the method being applicable to proliferation of any desired cells such as those mentioned above.

2. Cell Culture Substrate in which Cells are being Cultured

The cell culture substrate in which cells are being cultured is not particularly restricted so long as it is a substrate that allows growth (proliferation and differentiation) of the cells. While not a restriction, it may be selected from the group consisting of plates, dishes, culture plates, culture flasks, microwell plates and glass bottom dishes. The cell culturing surface in such cases will normally be flat, and according to the invention the porous polyimide film is contacted with the top surface of the cell culture substrate. Alternatively, it may be selected from the group consisting of microcarriers, silica porous bodies, cellulose sponges, nonwoven fabrics and hollow fibers. In such cases, one or more porous polyimide films may be contacted from either the top or bottom of the cell culture substrate, or both.

In the third mode described below, the first porous polyimide film in which cells are being cultured is itself the "cell culture substrate".

The specific steps for culturing of the cells in medium are not particularly restricted. It is possible to carry out the steps described throughout the present specification, or to employ any desired method suited for applying cells to a film-like substrate.

3. Porous Polyimide Film

The porous polyimide film to be used for the invention is the porous polyimide film described above.

While not a limitative feature, according to the invention, a cell culture substrate or cell-containing specimen is contacted with the surface of a porous polyimide film having a mesh structure with small holes having a mean pore size of no greater than 15 µm (A-surface).

Naturally, the porous polyimide film that is to be loaded with cells according to the invention is preferably in a state including no cells other than those that are to be loaded, i.e. a sterilized state. The method of the invention preferably includes a step of pre-sterilizing the porous polyimide film. A porous polyimide film has very excellent heat resistance and is lightweight, allows free selection of the shape and size, and is easy to treat for sterilization. Any desired sterilization treatment may be conducted, such as dry heat sterilization, steam sterilization, sterilization with a disinfectant such as ethanol, or electromagnetic wave sterilization using ultraviolet rays or gamma rays.

The cells that have been applied to the surface of the porous polyimide film can stably grow and proliferate on the surface and/or in the interior of the film. The cells may be in a variety of different forms, depending on the location of growth and proliferation in the film. According to one mode of the invention, growth may be carried out while moving the surface and interior of the porous polyimide film and changing the form, depending on the type of cells.

4. Migration of Cells from Cell Culture Medium to Porous Polyimide Film

Cells that have been grown on or inside different substrate including the plate, dish, culture plate, microcarrier, silica porous body, cellulose sponge or porous polyimide film itself, are contacted with a new porous polyimide film (which has a large growing area since no cells are growing in it), and this initiates migration from the substrate where the cells live to the porous polyimide film, whereupon contact for several hours to several days results in transfer and anchoring onto the empty porous polyimide film side. Since the migration is largely governed by the state of contact between the surfaces, more efficient migration can be achieved by increasing the effective contact area (essentially excluding the space). As proliferation can take place during the migration, the phenomenon is considered to be equivalent to subculturing of the cells.

For more efficient contact, a weight or fastener may be utilized to fix the porous polyimide film. A method of lifting the porous polyimide film up into the gas phase to widen the contact surface may also be employed. Although a method of removing the contacted porous polyimide film for culturing may be employed, culturing may instead be promoted while maintaining the state of contact.

When the cell culturing surface is flat, and the cell culture substrate is, for example, in a plate, dish, culture plate, culture flask, microwell plate or glass bottom dish, the porous polyimide film can be contacted with the top surface of the cell culture substrate. When the cell culturing surface is three-dimensional (spatial), and the cell culture substrate is, for example, in a microcarrier, silica porous body, cellulose sponge, nonwoven fabric or hollow fibers, one or more porous polyimide films may be contacted from above or below the cell culturing substrate, or both.

5. Cell Culturing

The method of the invention includes culturing cells after allowing the cells to migrate to a porous polyimide film.

Application of cells to a porous polyimide film and their culturing is described in PCT/JP2014/070407. Culturing methods suited for various cells including animal cells, plant cells and bacteria are publicly known, and a person skilled in the art may carry out culturing of cells on the porous polyimide film using any publicly known method. The cell culture medium may also be prepared as appropriate for the type of cells.

Cell culture methods and cell culture media for animal cells may be found in the Cell Culture Media Catalog of Lonza Group, Ltd., for example. Cell culture methods and cell culture media for plant cells may also be found in the Plant Tissue Culturing Media Series by Wako Corp., for example. Cell culture methods and cell culture media for bacteria may also be found in the General Bacterial Media Catalog of BD Corp., for example.

The cell culture using a porous polyimide film may be combined with another suspension culture support such as a microcarrier, cellulose sponge or the like.

Cell culturing can be classified into culturing where the cultured cells are adhesion culture-type cells or suspension culture-type cells, depending on the state in the cell culture. Adhesion culture-type cells are cultured cells that adhere and grow on a culturing vessel, with the medium being exchanged at the time of subculture. Suspension culture-type cells are cultured cells that grow in a suspended state in a medium, and generally the medium is not exchanged with each subculture but dilution culture is carried out. Because suspension culture allows culturing in a suspended state, i.e. in a liquid, mass culturing is possible, and because it is three-dimensional culturing, unlike with adherent cells that grow only on the culturing vessel surface, the advantage of increased culturable cell count per unit space is afforded.

According to the method of the invention, when the porous polyimide film is used in a state suspended in the cell culture medium, two or more fragments of the porous polyimide film may be used. Since the porous polyimide film is a flexible thin-film, using such fragments that are suspended in the culture solution, for example, allows a porous polyimide film with a large surface area to be added into a fixed volume of cell culture medium. In the case of normal culturing, the container base area constitutes the area limit in which cell culture can be accomplished, but with cell culturing using the porous polyimide film of the invention, all of the large surface area of the previously added porous polyimide film constitutes area in which cell culturing can be accomplished. The porous polyimide film allows the cell culture solution to pass through, allowing supply of nutrients, oxygen and the like even into the folded film, for example.

In the method of the invention, preferably the cells grow and proliferate on the surface or in the interior of the porous polyimide film. By the method of the invention it is possible to carry out continuous growth of cells for 5 days or longer, more preferably 10 days or longer and even more preferably 30 days or longer.

As one mode of the method of the invention, when the cultured cell count is high, a continuous culturing apparatus may be used in which the medium is added in a continuous manner. Since the medium is continuously added, it is possible to retain the mutually adhered state while maintaining a wet environment, and mobility and proliferation onto the empty porous polyimide film can thus be increased.

As one mode of the method of the invention, a porous polyimide film is contacted with a plate in which cells are being cultured, from the top of the culturing surface, and a stainless steel mesh or the like is placed over it while continuing the culturing for a certain period of time. Thereafter, the porous polyimide film is separated from the contact surface and culturing of the cells that have migrated into the film is continued.

V. Method of Culturing Cells by Allowing them to Migrate onto Porous Polyimide Film (Third Mode)

One mode of the invention is a method of culturing cells by allowing them to migrate onto a porous polyimide film, the method including contacting the top surface or bottom surface, or both, of a first porous polyimide film on which cells are being cultured, with a second porous polyimide film on which cells are not being cultured, to allow the cells to migrate from the first porous polyimide film to the second porous film, and culturing the cells that have been allowed to migrate to the second porous polyimide film. The cells migrate from a first porous polyimide film in which cells are being cultured, to a second porous polyimide film in which cells are not being cultured.

The definitions of "cells" and "porous polyimide film" are the same as those for the first and second modes.

There are also no particular limitations on the mode in which a first porous polyimide film and a second porous polyimide film are contacted. The film may be contacted from the top surface or bottom surface of the first porous polyimide film, or both. The first porous polyimide film may be a porous polyimide film that has been cryopreserved while holding the cells, in which case the porous polyimide film used may be thawed by any desired method which allows the cells to survive. This will allow the cells that have been preserved in a living state throughout freezing and thawing to be isolated into the second porous polyimide film, so that culturing can be continued.

Figure 2:
FIG. 2 is a schematic diagram showing "migration of cells from a porous polyimide film to an empty porous polyimide film", as one mode of the invention. A porous polyimide film in which cells have been cultured (first porous polyimide film) is sandwiched between both upper and lower empty porous polyimide films (second porous polyimide films) or either one, to prepare a layered aggregate. The prepared layered aggregate is submerged to the bottom of a culture plate, for example, using a stainless steel mesh and glass cube as weight, and both are contacted to allow migration of cells from the porous polyimide film in which the cells are growing to the empty film. During this time, the cells are not forcibly stripped off by physical pressing force but rather, they passively migrate by active movement of the cells.
Figure 5:
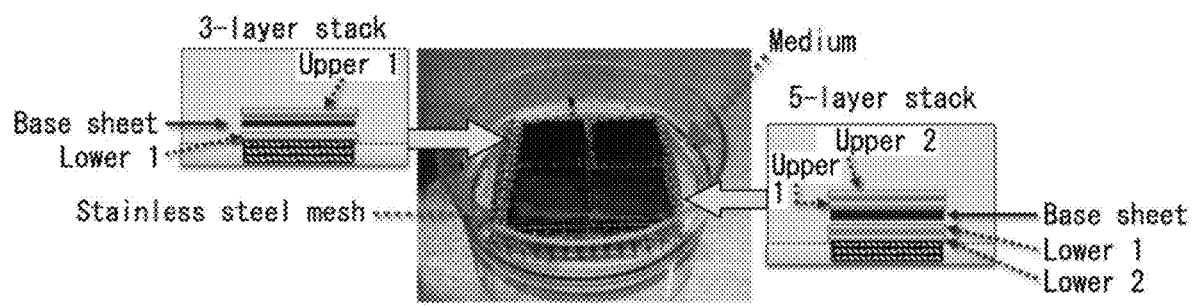
FIG. 5 shows a synoptic photograph of an experiment in Example 6, wherein porous polyimide films in which CHO cells are being cultured have a "3-layer structure" by sandwiching in contact with one upper and lower empty porous polyimide film each, and a "5-layer structure" by sandwiching in contact with two upper and lower empty porous polyimide films each.

For example, as shown in FIG. 2, the entire complex of the porous polyimide film in which cells have been grown, and an empty porous polyimide film, may be immersed in medium, and contacted together using a metal mesh or glass cube as a weight. While the first porous polyimide film and the second porous polyimide film are in a contacted state, the entire film aggregate may be lifted up into the gas phase. For example, as shown in FIG. 5, metal meshes may be layered to create a mounting frame, and the entire film aggregate of the porous polyimide film in which the cells have been grown and the empty porous polyimide film may be set on them, increasing the adhesiveness between the sheets and promoting migration of the cells between the sheets and proliferation thereof.

For each of these modes, two or more films may be used for both the empty porous polyimide film and the cell-grown porous polyimide film. For example, an aggregate of 30 films of each may be layered together, or multiple films may be layered with one each in an alternating manner. Also, sheets that have been cultured as an aggregate may be separated out one at a time and cultured.

In the layers, each porous polyimide film itself serves as a substrate for cell growth, and therefore it is important for the porous polyimide film used to be thoroughly wetted beforehand and to form an airless state.

The third mode may further include, prior to contacting the second porous polyimide film with the first porous polyimide film, a step of preparing the first porous polyimide film in which cells are being cultured, and specifically a step of applying cells to the empty first porous polyimide film in which cells are not being cultured, and culturing the cells in the first porous polyimide film.

There are no particular restrictions on the specific step for applying the cells onto the empty first porous polyimide film in which cells are not being cultured. It is possible to carry out the steps described throughout the present specification, or to employ any desired method suited for applying cells to a film-like support.

While not a restriction, there may be employed a method of allowing migration of cells into the porous polyimide film according to the second mode. Specifically, the empty first porous polyimide film is contacted with the cell culture substrate in which cells are being cultured, and the cells are allowed to migrate from the cell culture substrate to the porous polyimide film to apply the cells to the first porous polyimide film.

Alternatively, application of the cells to the porous polyimide film may be accomplished by any of the following modes as described in PCT/JP2014/070407, for example.

(A) A mode including a step of seeding cells on the surface of a porous polyimide film;

(B) A mode including a step of:

placing a cell suspension on the dried surface of the porous polyimide film, allowing it to stand, or moving the porous polyimide film to promote efflux of the liquid, or stimulating part of the surface to cause absorption of the cell suspension into the film, and retaining the cells in the cell suspension inside the film and allowing the water to flow out; and (C) A mode including a step of:

wetting one or both sides of the porous polyimide film with a cell culture solution or a sterilized liquid, loading a cell suspension into the wetted porous polyimide film, and retaining the cells in the cell suspension inside the film and allowing the water to flow out.

VI. Method of Culturing Cells by Allowing them to Migrate onto Porous Polyimide Film (Fourth Mode)

According to one mode of the invention, the method includes contacting a cell-containing biological sample with the top surface or bottom surface of a porous polyimide film, or both, to allow the cells to migrate from the biological sample to the porous polyimide film, and culturing the cells that have been allowed to migrate to the porous polyimide film. The cells migrate from the biological sample directly to the porous polyimide film.

The definitions of "cells" and "porous polyimide film" are the same as those for the first to third modes.

There are no particular restrictions on the "cell-containing biological sample". For example, it may include all or a portion of an organ or tissue that has been isolated from the body. Though not restrictive, this includes cell-containing biological samples derived from lungs, skin and liver.

This mode is a method of allowing migration and culturing of a highly mobile cell population all at once from a biological sample in which numerous different types of cells are growing in an integrated manner to a porous polyimide film, allowing difficult manipulations, such as recreating the environments of various biological organs, for example, to be accomplished in a convenient manner.

For this mode as well, a method may be employed in which the contact of the porous polyimide film with the biological sample is from the top surface or bottom surface, or both. When a specimen is to be contacted with the porous polyimide film, the method employed may be one in which a metal mesh or glass cube is used as a weight to immerse the specimen/porous polyimide film complex in the medium, or a method of raising it into a gas phase to contact the specimen and the porous polyimide film.

For any of modes 1 to 4 according to the invention, the migration of cells from a cell culture substrate in which cells are being cultured, a cell-containing biological sample or a porous polyimide film in which cells are being cultured, to a porous polyimide film in which cells are not being cultured, may be repeated two or more times. The method of the invention does not use trypsin or the like as in the prior art, but allows migration and subculturing of cells by a convenient method. The number of subcultures is not particularly restricted.

VII. Cell Culturing Apparatus

The invention also relates to a cell culturing apparatus for use in the method of the invention, the apparatus including a porous polyimide film. In the cell culturing apparatus of the invention, the porous polyimide film may be used in a fixed state, or it may be used in a floating state in the cell culture medium, and it may be either placed in the medium or exposed from the medium. In the cell culturing apparatus, two or more porous polyimide films may be layered either above and below or left and right. The layered aggregates or cluster may be either placed in the medium or exposed from the medium.

The cell culturing apparatus for cell culturing of the invention may be a known cell culturing apparatus, in any desired form so long as it includes a porous polyimide film. The shape and scale of the culturing apparatus is not particularly restricted, and any scale from a dish or test tube to a large tank may be used, as appropriate. These include, for example, Cell Culture Dish by BD Falcon, and Nunc Cell Factory by Thermo Scientific. By using a porous polyimide film according to the invention, it has become possible to carry out culturing even of cells that have not been capable of natural suspension culture, using an apparatus intended for suspension culture, in a state similar to suspension culturing. The apparatus for suspension culture that is used may be, for example, a spinner flask or rotating culturing flask by Corning, Inc. As an environment allowing a similar function to be obtained, there may be used a hollow fiber culturing system such as the FiberCell® System by Veritas.

The cell culturing apparatus for cultured cells according to the invention may be a continuous circulating or open apparatus, wherein medium is continuously added to and recovered from the films on the mesh, and the method may also be carried out with a type that exposes the porous polyimide films to air.

VIII. Kit for Use in Method of Culturing Cells while Allowing them to Migrate onto Porous Polyimide Film The invention further relates to a kit for use in a method of culturing cells of the invention while allowing them to migrate onto a porous polyimide film, the kit including a porous polyimide film.

The kit of the invention may include constituent elements necessary for cell culturing in addition to the porous polyimide film, as appropriate. This includes, for example, the cells to be applied to the porous polyimide film, the cell culture medium, the continuous culture medium-supply apparatus, the continuous culture medium-circulating apparatus, the scaffold or module for support of the porous polyimide film, the cell culturing apparatus, the sterilized plate or rectilinear plate for operation, the cell scraper for handling of the cell suspension, and the kit instruction manual.

While not restrictive, one mode includes a package containing either one or a plurality of sterilized porous polyimide films stored in a transparent pouch, in a form allowing their use for cell culturing, or a kit having a sterile liquid encapsulated together with a porous polyimide film in the same pouch, in the form of an integrated film/liquid allowing efficient suction seeding.

IX. Use

The invention further includes the use of a porous polyimide film for the method of the invention described above.

The present invention will now be explained in greater detail by examples. It is to be understood, however, that the invention is not limited to these examples. A person skilled in the art may easily implement modifications and changes to the invention based on the description in the present specification, and these are also encompassed within the technical scope of the invention. Unless otherwise specified, the term "porous polyimide film" refers to a porous polyimide film with a total film thickness of 25 µm and a porosity of 73%. Each porous polyimide film had at least two different surface layers (A-surface and B-surface), and a macro-void layer sandwiched between the two surface layers. The mean pore size of the holes in the A-surface was 6 µm, and the mean pore size of the holes in the B-surface was 46 µm.

The porous polyimide films used in the following examples were prepared by forming a polyamic acid solution composition including a polyamic acid solution obtained from 3,3',4,4'-biphenyltetracarboxylic dianhydride (s-BPDA) as a tetracarboxylic acid component and 4,4'-diaminodiphenyl ether (ODA) as a diamine component, and polyacrylamide as a coloring precursor, and performing heat treatment at 250° C. or higher.

Human mesenchymal stem cells (product code PT-2501, by Lonza)

HepG2 (HEPG2-500 by CET (Cellular Engineering Technologies, Inc.))

Human fibroblasts (product code CC-2511 by Lonza)

CHO-K1 (cat. 85051005 by Public Health England)

CHO DP-12 (ATCC CRL-12445)

MDCK (Public Health England cat. 85011435)

Human mesenchymal stem cell medium (product code Pt-3238, by Lonza)

HepG2 medium (cat. HEPG2.E. Media-450 by CET (Cellular Engineering Technologies, Inc.))

Human fibroblast medium (product code CC-3132 by Lonza)

CHO-K1 medium (Ham's F-12 087-08335 by Wako Pure Chemical Industries, Ltd.)

CHO DP-12 medium (IMDM 098-06465 by Wako Pure Chemical Industries, Ltd.)

MDCK medium (E-MEM 051-07615 by Wako Pure Chemical Industries, Ltd.)

3.5 cm dish (cat. 353001 by Falcon)

Cell Counting Kit 8 (CK04, Dojindo Laboratories)

Stainless steel mesh (60 mesh E9117 by Kyuho Corp., Japan)

2 cm×2 cm sterilized square vessel (cat. 103k by Thermo Fisher Scientific)

Penicillin-Streptomycin-Amphotericin B Suspension (X100) (161-23181 by Wako Pure Chemical Industries, Ltd.)

Microscope, image software LSM 700 by Carl Zeiss, software: ZEN

Example 1

Gas Phase Exposure of Cell-Grown Porous Polyimide Film (1)

After adding 1 ml of cell culture medium to a 2 cm×2 cm sterilized square vessel, five 1.4 cm-square sterilized porous polyimide films were each immersed therein with the A-surfaces of the mesh structure facing upward. After adding $4 \times 10^4$ human mesenchymal stem cells per sheet, cell culturing was carried out for 58 days with an incubator at 37° C., 5% $CO_2$, exchanging the medium twice a week, and the absorbance was measured using a CCK8.

Upon completion of the absorbance measurement, the medium was removed from the porous polyimide film in which the cells were growing and stored in an incubator for 24 hours. A CCK8 was again used to measure the absorbance, by which an absorbance of 1.0-fold (average) was confirmed.

Example 2

Gas Phase Exposure of Cell-Grown Porous Polyimide Film (2)

After adding 1 ml of cell culture medium to a 2 cm×2 cm sterilized square vessel, five 1.4 cm-square sterilized porous polyimide films were each immersed therein with the A-surfaces of the mesh structure facing upward. After adding $4 \times 10^4$ HepG2 cells per sheet, cell culturing was carried out for 31 days and the absorbance was measured using a CCK8.

Upon completion of the absorbance measurement, the medium was removed from the porous polyimide film in which the cells were growing and stored in an incubator for 24 hours. A CCK8 was again used to measure the absorbance, by which an absorbance of 1.1-fold (average) was confirmed.

Example 3

Migration from Porous Polyimide Film to Empty Porous Polyimide Film (1) Gas Phase Subculturing: 1

After adding 1 ml of cell culture medium to a 2 cm×2 cm sterilized square vessel, a 1.4 cm-square sterilized porous polyimide film was immersed therein with the A-surfaces of the mesh structure facing upward. After adding $5.2 \times 10^4$ human skin fibroblasts per sheet, cell culturing was carried out for 6 days and the cell count at the 6th day was measured using a CCK8.

The base sheet in which the cells were growing was sandwiched by an upper and a lower empty porous polyimide film. The upper and lower porous polyimide films were layered with their A-surfaces adhering to the base sheet. This state was continued for 24 hours, with the stainless steel mesh immersed down to the plate bottom and the aggregate of sheets exposed in air. Next, each sheet was isolated, 1 ml of cell culture medium was added in a 2 cm×2 cm sterilized square vessel, and culturing was continued. At the start of separation and 5 days thereafter, a CCK8 was used to measure the cell counts, and the growth behavior was observed. Anchoring and proliferation of the cells in each sheet were confirmed (FIG. 1).

Example 4

Migration from Porous Polyimide Film to Empty Porous Polyimide Film (2) Liquid Contact Method After adding 1 ml of cell culture medium to a 2 cm×2 cm sterilized square vessel, 1.4 cm-square sterilized porous polyimide films were each immersed therein with the A-surfaces of the mesh structure facing upward. After adding $5.2 \times 10^4$ human skin fibroblasts per film, cell culturing was carried out for 28 days and the cell count was periodically measured using a CCK8.

A film in which cells were growing was sandwiched by an upper and a lower porous polyimide film with the empty sheet side of the A-surfaces of the mesh structure as the contact surface, a 2 cm×2 cm stainless steel mesh and four 2-millimeter-square glass cubes were used as weights, and culturing was carried out for 14 days (FIG. 2).

Figure 3:
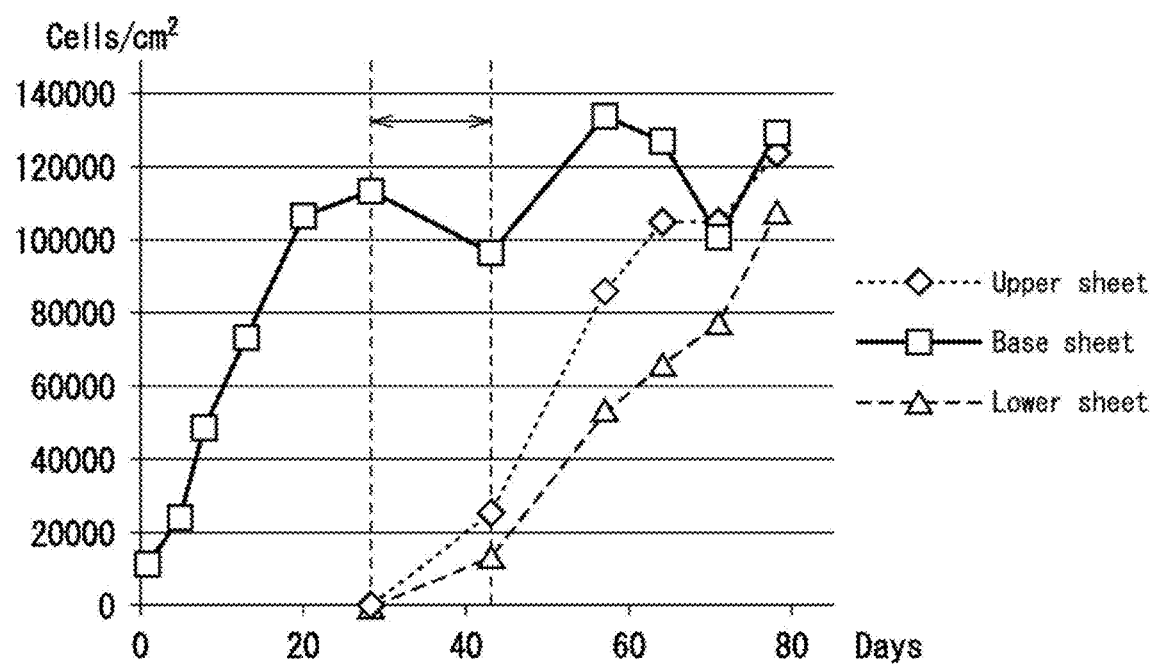
FIG. 3 shows the results of examining migration of cells in Example 4, when a porous polyimide film in which human skin fibroblasts are being cultured is sandwiched in contact with one upper and lower empty porous polyimide film each and submerged in medium, using weights.

After then removing the weights, each film was isolated and continuously cultured in an environment with 1 ml of cell culture medium added in a 2 cm×2 cm sterilized square vessel. After 14 days, 21 days, 28 days and 35 days, a CCK8 was used to measure the cell counts and observe the growth behavior. Both the original upper film and the lower set film were confirmed to have proliferation to cell counts near the upper limit of culturing (FIG. 3).

In an actual case of culturing by the same mode as described above, upon verifying the cell behavior by fluorescent visualization, the cells were confirmed to have actively migrated to the layered empty films with the passage of time. It was verified at least that migration of the cells had not occurred by physical scraping.

Example 5

Migration of Cells Grown on Plate Surface to Porous Polyimide Film

After seeding $2.0 \times 10^3$ HepG2 cells in a 3.5 cm-diameter plate, they were cultured for 33 days in a $CO_2$ incubator while exchanging the medium twice a week.

Figure 4:
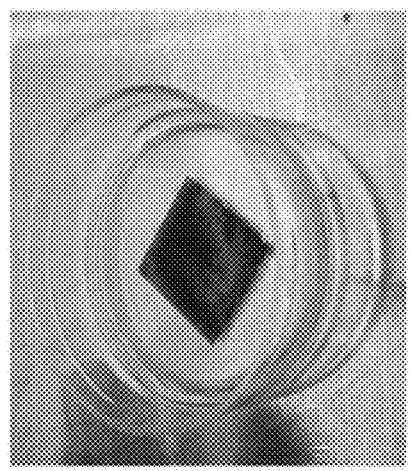
FIG. 4 shows an example of cell culturing using minimal medium. The medium is removed from the porous polyimide film in which cell culturing is being carried out in the plate. With the medium essentially absent from the plate, the plate is then returned to the incubator and culturing is continued.
Figure 4:
Figure 4:
Figure 4:
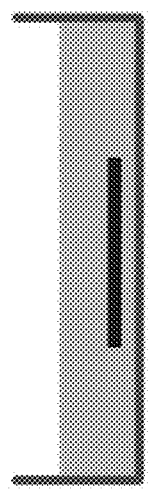

In the same plate there was floated in the medium a 1.4 cm-square sterilized square porous polyimide film with the A-surfaces of the mesh structure facing downward. The medium was gradually removed, with removal of the medium being stopped when the porous polyimide film just contacted the bottom surface (FIG. 4). Maintaining this state, the plate was transferred into an incubator and cultured for 24 hours. When after 24 hours, medium was gradually added, the porous polyimide film was moved and the cell count was measured using a CCK8, $1.2 \times 10^6$ cells were found to have grown over the entire sheet.

Example 6

Figure 6:
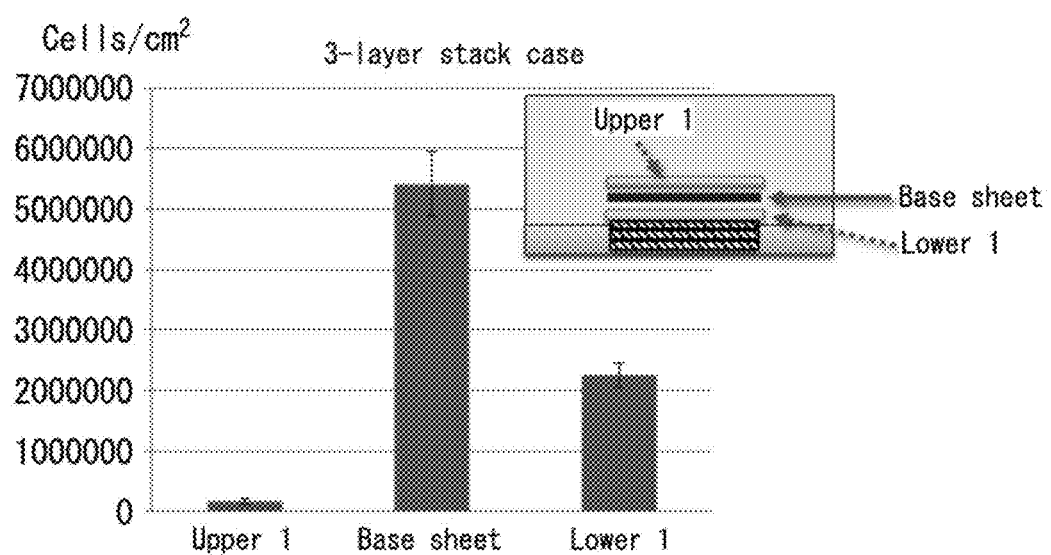
FIG. 6 shows the results of growing cells in Example 6, wherein porous polyimide films in which CHO cells are being cultured have a "3-layer structure" by sandwiching in contact with one upper and lower empty porous polyimide film each.
Figure 7:
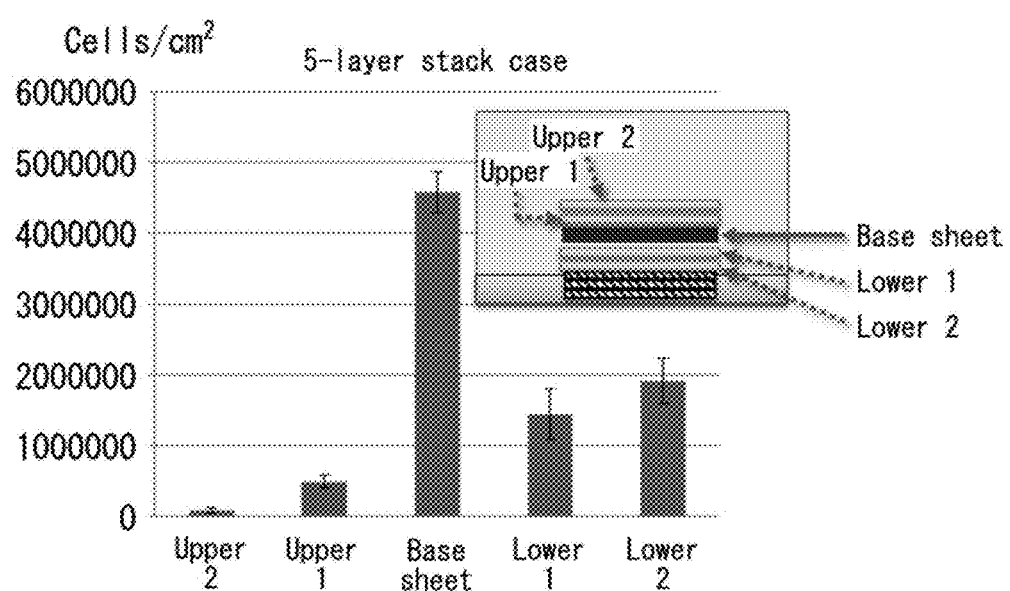
FIG. 7 shows the results of growing cells in Example 6, wherein porous polyimide films in which CHO cells are being cultured have a "5-layer structure" by sandwiching in contact with two upper and lower empty porous polyimide films each.

Migration from Porous Polyimide Film to Empty Porous Polyimide Film (3) Gas Phase Subculturing Method After adding 1 ml of cell culture medium to a 2 cm×2 cm sterilized square vessel, nine 1.4 cm-square sterilized porous polyimide films were each immersed in the medium with the A-surfaces of the mesh structure facing upward. After adding $4 \times 10^4$ CHO-K1 cells per sheet, cell culturing was carried out in a $CO_2$ incubator for 8 days, resulting in nearly the maximum growth state. The number of viable cells per sheet on the 8th day was $1.2 \times 10^7$ (average). After removing 5 of the sheets, each sheet was sandwiched with a new upper and lower porous polyimide film of the same size to prepare 5 sets of porous polyimide film stacks each with a 3-layer structure. Similarly, 4 of the sheets in which the cells had grown were removed, and each sheet was sandwiched with two new upper and lower porous polyimide films of the same size to prepare 4 sets of porous polyimide film stacks each with a 5-layer structure (FIG. 5). The total of 9 sets, including stacks with a 3-layer structure and a 5-layer structure, were placed on a mesh set in the medium, in contact with a gas phase, and culturing was continued. After continuing the culturing for 4 days, each stack was separated into the individual films and the cell count of each porous polyimide film was measured using a CCK8. Migration and proliferation of cells was confirmed in the stack interiors, with both the 3-layered stack (FIG. 6) and the 5-layered stack (FIG. 7). Favorable proliferation and migration of the cells was confirmed in the environment contacting the gas phase.

Example 7

Figure 8:
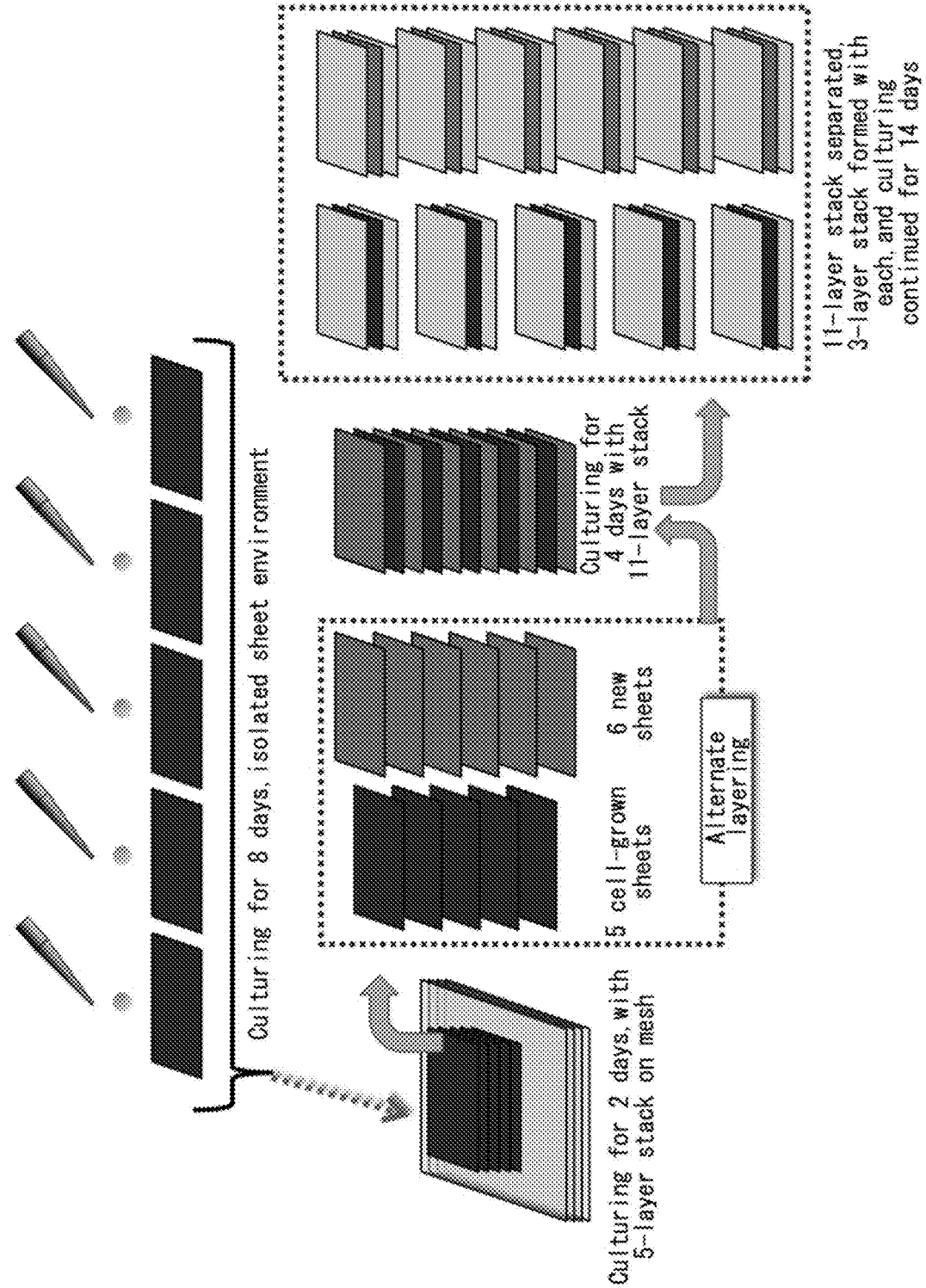
FIG. 8 shows a conceptual drawing of the experiment in Example 7, wherein porous polyimide films in which cells are being cultured are multiply layered in different forms and cells are subcultured and grown.

Migration from Porous Polyimide Film to Empty Porous Polyimide Film (4) Stepwise Subculturing After adding 1 ml of cell culture medium to a 2 cm×2 cm sterilized square vessel, five 1.4 cm-square sterilized porous polyimide films were immersed in the medium with the A-surfaces of the mesh structure facing upward. After adding $4×10^4$ CHO cells to each sheet, cell culturing was carried out in a $CO_2$ incubator for 8 days, and five were stacked for continued culturing in the medium for another 2 days. Medium exchange was performed at a pace of twice a week throughout the entire culturing period. On the 10th day, six new sterilized 1.4 cm-square porous polyimide films in which cells were not growing were prepared, and alternately stacked with the five sheets on which the CHO cells had been cultured, to prepare a stack with a total of 11 porous polyimide films. The prepared stack was placed on a mesh disposed in medium, in contact with a gas phase, and this state was maintained for 4 days. Next, the 11 sheets in which cells were growing were separately isolated, and each sheet was sandwiched with a new upper and lower porous polyimide film of the same size to prepare 11 sets of porous polyimide film stacks each with a 3-layer structure (FIG. 8).

The total of 11 sets of stacks each with a 3-layer structure were placed on a mesh set in the medium, in contact with a gas phase, and culturing was continued. Medium exchange was carried out as appropriate at a frequency of twice a week. Culturing was continued for 2 weeks with the 3-layer structures in a form in contact with a gas phase, similar to that described above. In the final 3-layer stacks, the interlayer sheets and lower sheets had reached a nearly saturated state by 2 weeks of culturing, with average mean cell counts of $9.5×10^6$ cells in the interlayer sheet and $9.1×10^6$ cells in the lower level sheet. The number of live cells in the upper layer sheet was $1.5×10^6$. With the multilayer stacks as well, it was confirmed that contact on the surface of each porous polyimide film had allowed sufficient migration of cells and promoted subculturing and proliferation.

Example 8

Mass Culturing with Gas Phase Exposure (1)

For this example, CHO-K1 cells were used for seeding in porous polyimide films, and then mass continuous culturing was carried out using a continuous culturing apparatus.

Figure 9:
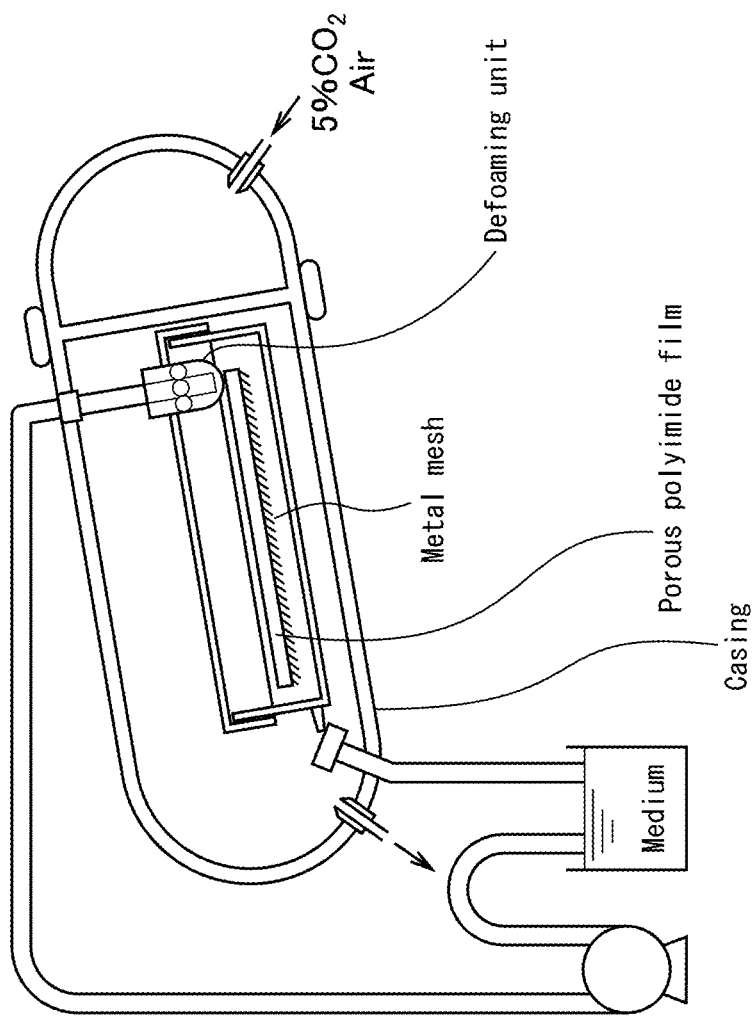
FIG. 9 shows an example of culturing with only a support using a medium-supply apparatus. By mounting layered cell-seeded porous polyimide films on a metal mesh and continuously or intermittently adding medium onto them, it is possible to carry out continuous culturing of the cells. Since the cells are cultured without pooling of the medium, it is possible to carry out culturing of the cells with a very high volume in a small space, while using a simple apparatus. Also shown is a defoaming unit for removal of bubbles that may interfere with cell culturing, or a nonwoven fabric or casing to prevent drift current on the surface, for the actual implementation.
Figure 9:
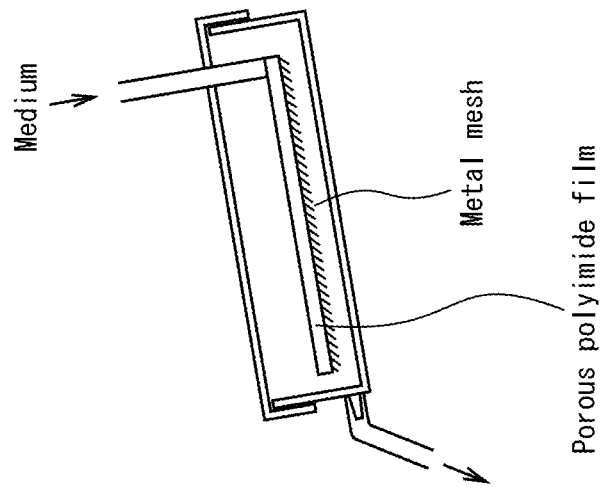

Ten 4 cm×10 cm sterilized porous polyimide films were subjected to dry heat sterilization, and arranged in a sterilized rectilinear dish. A suspension was prepared including $1.1×10^7$ CHO-K1 cells per 5 ml of medium (of which $1.1×10^7$ were viable cells and $5.0×10^5$ were dead cells, for a viable cell rate of 96%), and 0.5 ml was seeded into each of the previously prepared porous polyimide films. Each suspension placed on the sheets was homogenized with a cell scraper, and the solution was caused to pass through by slightly moving the sheets, thereby seeding the cells into the porous polyimide films. The 10 sheets were placed on a stainless steel metal mesh of the same size, a PE/PP-mixed nonwoven fabric was placed over it, and the aggregate including the cells was set in a plastic case (FIG. 9). The layered porous polyimide films including the cells were inclined approximately 20° at this time. Medium (Ham's F-12 containing penicillin/streptomycin/amphotericin B with addition of 10% FBS) was continuously added from the top end of the incline, and circulated from a 150 ml volume medium reservoir at a flow rate of 3 ml/min. The porous polyimide films were present as a mutually bonded aggregate.

Figure 10:
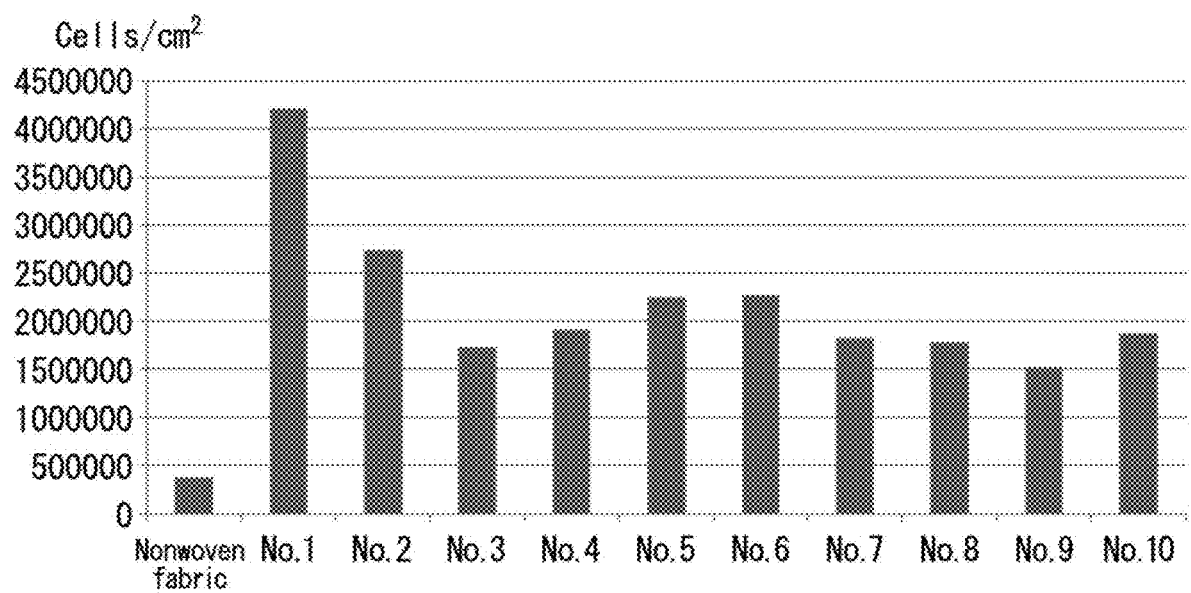
FIG. 10 shows the results after 5 days of culturing with a continuous culturing apparatus as illustrated in the conceptual drawing of FIG. 9, based on the state of growth of the cells for each sheet. The numbers on the abscissa refer to the numbers of the laminated sheets counting from the top.
Figure 11:
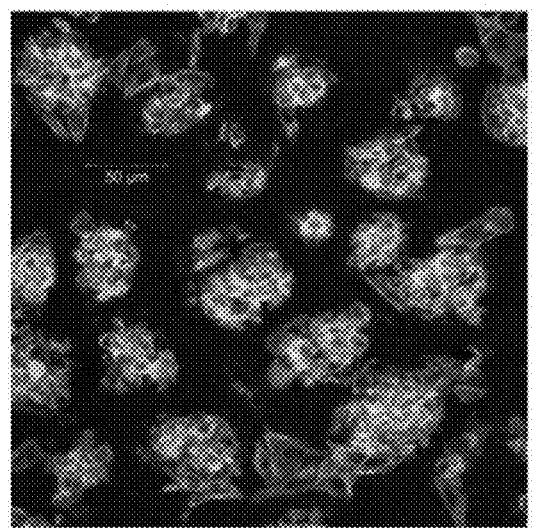
FIG. 11 is a fluorescent microscope photograph showing the results of culturing CHO-K1 cells using a cell culturing apparatus of the invention.

After 3 days, the solution of the medium reservoir was discarded, 100 ml of fresh medium solution was added to the medium reservoir, and circulation of the medium was continued for another 2 days. After 5 days from completion of the seeding, the medium circulation was halted and color reaction with CCK8 was used to determine the viable cell count. The total sum of the viable cells on each of the porous polyimide film sheets was $8.9×10^8$. The cell growth on the nonwoven fabric was $1.5×10^7$, and the viable cell density was $3.8×10^6$ per milliliter. The number of live cells per sheet are shown (FIG. 10: sheet numbers are counted from the top). The cell-grown porous polyimide films were partially cut out and fixed with formalin, staining was performed of the nuclei (DAPI), cell membranes (cell mask) and actin (phalloidin), and then a fluorescent microscope photograph was taken as shown in FIG. 11.

Example 9

Mass Culturing with Gas Phase Exposure (2)
Mass Continuous Culturing of Conditioned CHO-K1 Cells Using Porous Polyimide Films Ten 4 cm×10 cm-square porous polyimide films were subjected to dry heat sterilization at 180° C. for 30 minutes, and placed on a sterilizing plate with the A-surfaces of the mesh structure facing upward. Separately, 5 ml of a CHO-K1 cell suspension was prepared with the 0.5% FBS-conditioned CHO-K1 cells suspended at $2.4×10^6$ cells per milliliter of medium (of which $2.3×10^6$ were viable cells and $9.0×10^4$ were dead cells, for a viable cell rate of 96%). A 0.5 ml portion of the cell suspension was added to each of the 10 sterilized porous polyimide films, and leveled with a cell scraper. After standing for several minutes, the sheets were slightly moved to cause the suspension to pass through, after which the 10 cell-seeded sheets were layered on a metal mesh of the same shape as the sheets. A nonwoven fabric was then placed over the layered sheets and set inside the culturing apparatus, the culture medium supply line was installed at the top, and then the entire culturing apparatus was transferred to a forced aerated $CO_2$ incubator by Tietech Co., Ltd. set to 37° C., thus completing preparation for culturing.

A 150 ml portion of 0.5% FBS-containing Ham medium was circulated at a pace of 1 ml/min, and continuous culturing was initiated. After 3 days, the medium was removed and replaced with 100 ml of fresh medium, and culturing was continued for another 9 days while continuing medium exchange at the same pace.

Figure 12:
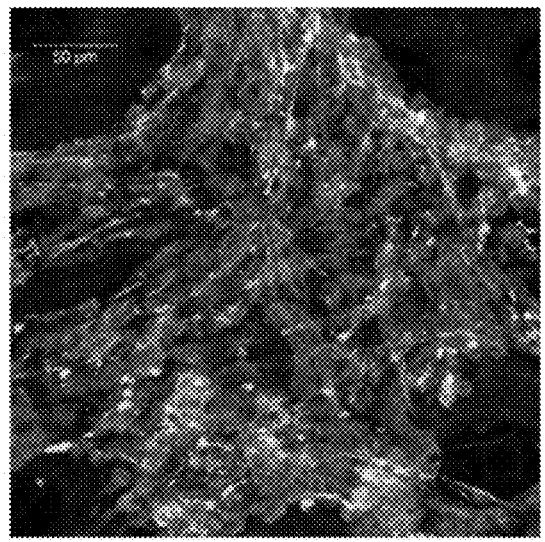
FIG. 12 is a fluorescent microscope photograph showing the results of culturing conditioned CHO-K1 cells using a cell culturing apparatus of the invention.

Circulation of the medium was halted on the 12th day from the start of culturing, and the porous polyimide films and nonwoven fabric were removed. The cell count of the removed porous polyimide films, as the aggregate, was determined with CCK8, and a total count of $2.6 \times 10^8$ cells was confirmed. The estimated cell culturing density was $1.7 \times 10^8$/ml. The cell-grown porous polyimide films were partially cut out and fixed with formalin, staining was performed of the nuclei (DAPI), cell membranes (cell mask) and actin (phalloidin), and then a fluorescent microscope photograph was taken as shown in FIG. 12. Satisfactory cell growth was confirmed even when using conditioned cells.

Example 10

Mass Culturing with Gas Phase Exposure (3): Mass Subculturing

Following Example 9, ten 4 cm×10 cm-rectangular porous polyimide films, with CHO-K1 cells adhering, were used as base sheets, and ten sterilized porous polyimide films of the same size were layered on the top surfaces of the base sheets with all of the A-surfaces of the mesh structures facing upward. Similarly, ten porous polyimide films were layered on the bottom surface of the base sheets with all of the A-surfaces of the mesh structure facing upward. A nonwoven fabric was then placed over the 30 layered sheets and set inside the culturing apparatus used in Example 9 (FIG. 9), the culture medium supply line was installed at the top, and then the entire culturing apparatus was transferred to a forced aerated $CO_2$ incubator by Tietech Co., Ltd. set to 37° C., thus completing preparation for culturing.

Figure 13:
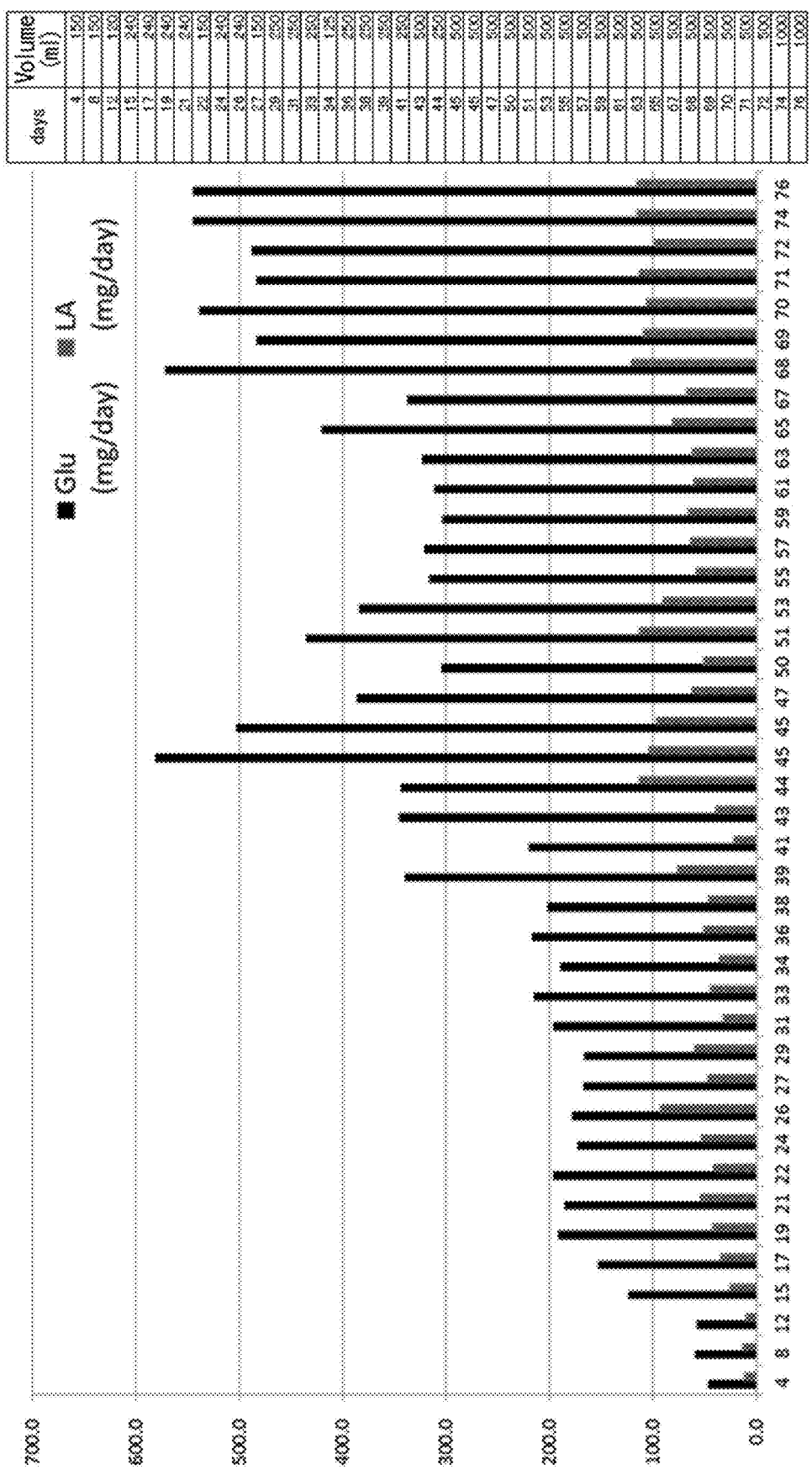
FIG. 13 is a graph showing the results of culturing for CHO-K1 cells using the cell culturing apparatus of the invention.

Next, 0.5% FBS-containing Ham medium was circulated at a pace of 2 ml/min, and continuous culturing was initiated. Culturing was continued for another 76 days or longer while continuing to exchange the medium at the pace shown at right in FIG. 13. The graph shows the number of days cultured and the amount of medium used. The glucose consumption and lactic acid production during this time were measured by LC/MS (Shimadzu LCMS-2020). The results are shown in FIG. 13.

Example 11

Migration from Porous Polyimide Film to Empty Porous Polyimide Film (5) Gas Phase Subculturing Method After adding 1 ml of medium to a 2 cm×2 cm sterilized square vessel, forty 1.4 cm-square sterilized porous polyimide films were immersed in the medium with the A-surfaces of the mesh structure facing upward. After adding a $2 \times 10^4$ MDCK cell suspension to the top of each sheet, cell culturing was carried out in a $CO_2$ incubator. Cell culturing was continued for 61 days while periodically observing the growth state of the cells. The cell count reached maximum by the 8th day, after which a stabilized cell count was maintained. The number of viable cells per sheet on the 61st day was $2.5 \times 10^6$ (average).

Figure 14:
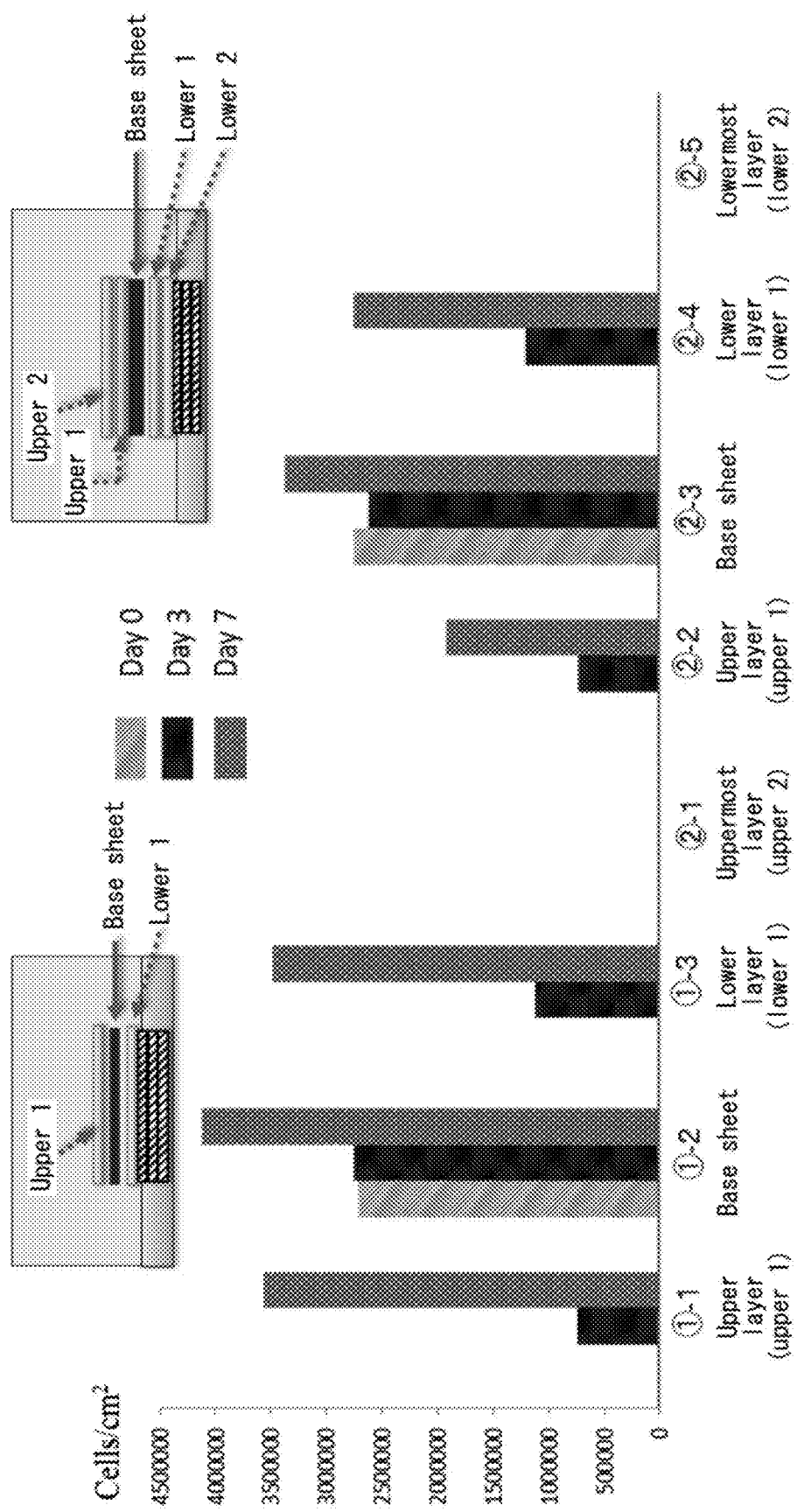
FIG. 14 is a graph showing the results of culturing MDCK cells by the method of the invention.

After removing one of the sheets, it was sandwiched with a new upper and lower porous polyimide film of the same size to prepare a set of stacked porous polyimide films with a 3-layer structure. After similarly removing one of the sheets on which cells had grown, it was sandwiched with two new upper and lower porous polyimide films each of the same size to prepare a set of stacked porous polyimide films with a 5-layer structure (FIG. 5). The total of 2 sets, including stacks with a 3-layer structure and a 5-layer structure, were placed on a mesh set in the medium, in contact with a gas phase, and culturing was continued in a $CO_2$ incubator. After 3 days, each stack was separated into the individual films and the cell count of each porous polyimide film was measured using a CCK8. Migration and proliferation of cells was confirmed inside both the 3-layer stack and the 5-layer stack, with a cell count equivalent to maximum being reached after one week. It was confirmed that contact with a gas phase resulted in efficient and rapid subculturing of the cells (FIG. 14).

Example 12

Migration from Porous Polyimide Film to Empty Porous Polyimide Film (6) Gas Phase Culturing Following Prolonged Culturing Confirming Proliferation by Gas Phase Subculturing after Prolonged Culturing of Human Skin Fibroblasts After adding 2 ml of medium to a 6 cm-diameter plate, human skin fibroblasts were seeded on the A-surfaces of the mesh structures of 1.4 cm-square sterilized porous polyimide films, at $4 \times 10^4$ cells per sheet, and culturing was carried out for 1 month. The sheets were then cut into quarter portions and culturing was continued for a total of 230 days of culturing. Next, three 1.4 cm-square stainless steel meshes were stacked and set at the center of a 3.5 cm dish, and the porous polyimide film was placed thereover and sandwiched with two empty 1.4 cm-square sterilized porous polyimide films. When 1 ml of medium was added in this state, the medium reached approximately the height of the sheets. They were then directly moved into a $CO_2$ incubator, the medium was exchanged at a rate of twice per week, and cell culturing was subsequently continued.

After 7 days of culturing, each sheet was separately isolated and culturing was continued in each sheet. After 7, 10, 16, 21, 28, 42 and 56 days the cell counts were measured using a CCK8, and the cell growth behaviors on the original sheets and the subsequently set empty porous polyimide films were observed with a CCK8, based on staining. The behavior was observed whereby the cells efficiently migrated from the porous polyimide films in which prolonged culturing of human skin fibroblasts had taken place, to the empty porous polyimide films, and continuously proliferated. The results are shown in FIG. 15.

ELISA measurement was performed, for a human skin fibroblast-cultured sheet wherein continuous prolonged culturing had been carried out for 294 days on a porous polyimide film without gas phase subculturing, and a base sheet that had been gas-phase subcultured for the same period up to the 230rd day and two sheets (upper and lower) that had been cultured by gas phase culturing for 56 days after subculturing, and the fibronectin produced by the living human skin fibroblasts was compared with the amount of fibronectin released in 24 hours into the medium in which the sheets had been cultured. Stable production of fibronectin was confirmed without any effect of the culturing period or gas phase subculturing. The results are shown in Table 2. For comparison, the fibronectin amount produced from two sheets cultured for 13 days with a porous polyimide film was also recorded.

TABLE 2

| Entry (days cultured and condition) | Fibronectin production per unit area (ng/cm²/day) |
|---|---|
| Porous polyimide film, normal culturing, day 13 (Run 1) | 480 |
| Porous polyimide film, normal culturing, day 13 (Run 2) | 376 |

TABLE 2-continued

| Entry (days cultured and condition) | Fibronectin production per unit area (ng/cm²/day) |
|---|---|
| 294 day-cultured sheet (no gas phase subculturing) | 760 |
| 294 day-cultured sheet (gas phase-subcultured base sheet) | 709 |
| 56 day-cultured sheet after gas phase subculturing (top) | 338 |
| 56 day-cultured sheet after gas phase subculturing (bottom) | 266 |

What is claimed is:

1. A method of culturing cells, the method including:
(1) contacting a first porous polyimide film with a cell-containing sample, to allow the cells to migrate from the cell-containing sample onto the first porous polyimide film; and
(2) culturing the cells that have been allowed to migrate onto the first porous polyimide film,
wherein the first porous polyimide film has a multilayer structure having at least two surface layers (an A-surface and a B-surface), and a macro-void layer sandwiched between the two surface layers,
a mean pore size of the holes in the A-surface is smaller than a mean pore size of the holes in the B-surface, and
the macro-void layer has a partition bonded to the surface layers (the A-surface and the B-surface), and a plurality of macro-voids, wherein each of the macro-voids is surrounded by the partition and the surface layers (the A-surface and the B-surface).

2. The method according to claim 1, wherein the cell-containing sample is a cell culture substrate in which cells are being cultured, and wherein the cell culture substrate is selected from the group consisting of plates, dishes, culture plates, culture flasks, microwell plates and glass bottom dishes, and the first porous polyimide film is contacted with the top surface of the cell culture substrate.

3. The method according to claim 1, wherein the cell-containing sample is a cell culture substrate in which cells are being cultured, and wherein the cell culture substrate is selected from the group consisting of microcarriers, silica porous bodies, cellulose sponges, nonwoven fabrics and hollow fibers, and one or more first porous polyimide films are contacted with the cell culture substrate from the top, bottom or both.

4. The method according to claim 1, wherein the cell-containing sample is a cell-containing biological sample.

5. The method according to claim 1, wherein the cell-containing sample is a second porous polyimide film in which cells are being cultured, and wherein the step (1) is a step of contacting the first porous polyimide film with the top surface or bottom surface, or both, of the second porous polyimide film in which cells are being cultured,
wherein the second porous polyimide film has a multilayer structure having at least two surface layers (an A-surface and a B-surface), and a macro-void layer sandwiched between the two surface layers,
a mean pore size of the holes in the A-surface is smaller than a mean pore size of the holes in the B-surface, and
the macro-void layer has a partition bonded to the surface layers (the A-surface and the B-surface), and a plurality of macro-voids, wherein each of the macro-voids is surrounded by the partition and the surface layers (the A-surface and the B-surface).

6. The method according to claim 5, wherein the step (1) is a step of contacting the first porous polyimide film with the second porous polyimide film in which cells are being cultured, in a liquid phase, and then lifting the film aggregate up into a gas phase from the liquid phase.

7. The method according to claim 5, wherein the second porous polyimide film in which cells are being cultured is obtained by applying cells to the second porous polyimide film in which cells are not being cultured, and culturing the cells on the second porous polyimide film.

8. The method according to claim 7, wherein the second porous polyimide film in which cells are being cultured is obtained by contacting the second porous polyimide film in which cells are not being cultured with the cell-containing sample, to allow the cells to migrate from the cell-containing sample to the second porous polyimide film.

9. The method according to any one of claim 1, wherein the first porous polyimide film is a porous polyimide film including a polyimide obtained from a tetracarboxylic dianhydride and a diamine.

10. The method according to claim 9, wherein the first porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

11. The method according to claim 1, wherein a mean pore size of the A-surface is 0.01 μm to 15 μm.

12. The method according to claim 1, wherein a mean pore size of the B-surface is 20 μm to 100 μm.

13. The method according to claim 1, wherein a mean pore size of the macro-void layer is 10 μm to 500 μm in the planar direction of the first polyimide film.

14. The method according to claim 1, wherein the film thickness of the first porous polyimide film is no greater than 75 μm.

15. The method according to claim 1, wherein two or more first porous polyimide films to which the cells have migrated are layered either above and below or left and right in the cell culture medium, and the cells are cultured.

16. The method according to claim 1, which includes repeating two or more times the procedure of allowing the cells to migrate from the cell-containing sample, to the first porous polyimide film in which cells are not being cultured.

17. A method of culturing cells, the method including:
contacting a porous polyimide film with a cell culture substrate in which cells are being cultured or a cell-containing biological sample, to allow the cells to migrate from the cell culture substrate in which cells are being cultured or the cell-containing biological sample, onto the porous polyimide film; and
culturing the cells that have been allowed to migrate onto the porous polyimide film,
wherein the porous polyimide film has a multilayer structure having at least two surface layers (an A-surface and a B-surface), and a macro-void layer sandwiched between the two surface layers,
a mean pore size of the A-surface is 0.01 μm to 15 μm, and a mean pore size of the B-surface is 20 μm to 100 μm, and a mean pore sizes of the macro-void layer is 10 to 500 μm in the planar direction of the polyimide film,
the macro-void layer has a partition bonded to the surface layers (the A-surface and the B-surface), and a plurality of macro-voids, wherein each of the macro-voids is surrounded by the partition and the surface layers (the A-surface and the B-surface), and the film thickness of the porous polyimide film is no greater than 75 μm.

* * * * *